US012768845B2

(12) United States Patent
Kim et al.

(10) Patent No.: US 12,768,845 B2
(45) Date of Patent: Oct. 20, 2026

(54) TWO-PHOTON FLUORESCENT PROBE COMPOUND SELECTIVE FOR AMYLOID BETA PLAQUES AND METHOD FOR IMAGING AMYLOID BETA PLAQUES USING SAME

(71) Applicant: Korea University Research and Business Foundation, Seoul (KR)

(72) Inventors: Jong Seung Kim, Seoul (KR); Jinwoo Shin, Seoul (KR); Peter Verwilst, Seoul (KR); Dokyoung Kim, Seoul (KR); Inhee Mook-Jung, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 988 days.

(21) Appl. No.: 17/802,233

(22) PCT Filed: Jan. 26, 2021

(86) PCT No.: PCT/KR2021/001002
§ 371 (c)(1),
(2) Date: Aug. 25, 2022

(87) PCT Pub. No.: WO2021/172769
PCT Pub. Date: Sep. 2, 2021

(65) Prior Publication Data
US 2023/0099969 A1 Mar. 30, 2023

(30) Foreign Application Priority Data
Feb. 26, 2020 (KR) ........................ 10-2020-0023888

(51) Int. Cl.
*G01N 33/68* (2006.01)
*C07D 311/16* (2006.01)
(Continued)

(52) U.S. Cl.
CPC ....... *G01N 33/6896* (2013.01); *C07D 311/16* (2013.01); *C07D 311/58* (2013.01);
(Continued)

(58) Field of Classification Search
CPC ................ C07D 311/16; C07D 311/58; G01N 33/6896; G01N 2333/4709; G01N 2800/2821
See application file for complete search history.

(56) References Cited

U.S. PATENT DOCUMENTS 10,149,644 B2 12/2018 Ran et al.
2020/0079762 A1* 3/2020 Aguilera-Iparraguirre .................. C07D 405/14
2023/0099969 A1* 3/2023 Kim .................. G01N 21/6458 436/86

FOREIGN PATENT DOCUMENTS

EP 0005172 B1 * 4/1981 ........... C07D 311/16
KR 10-2014-0049370 A 4/2014
(Continued)

OTHER PUBLICATIONS

Murakami, M. et al. "Photoinduced Electron Transfer in Photorobust Coumarins Linked with Electron Donors Affording Long Lifetimes of Triplet Charge-Separated States," ChemPhysChem 2010, 11, 2594-2605 and Supporting Information (Year: 2010).*
(Continued)

*Primary Examiner* — Jennifer Wecker
*Assistant Examiner* — Michelle Adams
(74) *Attorney, Agent, or Firm* — Sughrue Mion, PLLC

(57) ABSTRACT

The present invention relates to a two-photon fluorescent probe compound that is a coumarin or an iminocoumarin, and a method for imaging amyloid beta plaques using same, wherein the two-photon fluorescent probe compound according to the present invention maintains an excellent two-photon fluorescence cross-section while at the same time maintaining efficient BBB permeability by minimizing
(Continued)

background fluorescence such that a high signal-to-noise ratio is exhibited, and can effectively image Aβ plaques since high selectivity and sensitivity to Aβ plaques are exhibited, and can thus be usefully used in the field of neurodegenerative disease research, including early diagnosis and treatment of Alzheimer's disease.

5 Claims, 18 Drawing Sheets

(51) Int. Cl.

| | |
|---|---|
| ***C07D 311/58*** | (2006.01) |
| ***C07D 407/04*** | (2006.01) |
| ***G01N 21/64*** | (2006.01) |
| ***G01N 33/58*** | (2006.01) |

(52) U.S. Cl.

CPC ....... *C07D 407/04* (2013.01); *G01N 21/6428* (2013.01); *G01N 33/582* (2013.01); *G01N 21/6458* (2013.01); *G01N 2333/4709* (2013.01); *G01N 2800/2821* (2013.01)

(56) References Cited

FOREIGN PATENT DOCUMENTS

| | | | |
|---|---|---|---|
| KR | 10-2015-0002110 | A | 1/2015 |
| KR | 10-2016-0049819 | A | 5/2016 |
| KR | 10-2016-0087688 | A | 7/2016 |
| KR | 10-2017-0110496 | A | 10/2017 |

OTHER PUBLICATIONS

Jinwoo Shin, et al., "Harnessing Intramolecular Rotation To Enhance Two-photon Imaging of Ab Plaques through Minimizing Background Fluorescence", Angewandte Chemie International Edition, 2019, 58, pp. 5648-5652 ; first published Feb. 26, 2019.

International Search Report for PCT/KR2021/001002 dated May 28, 2021.

Korean Office Action for Korean Application No. 10-2020-0023888 dated Sep. 26, 2021, 3 pages.

Written Opinion for PCT/KR2021/001002 dated May 28, 2021.

* cited by examiner

[Fig. 1]
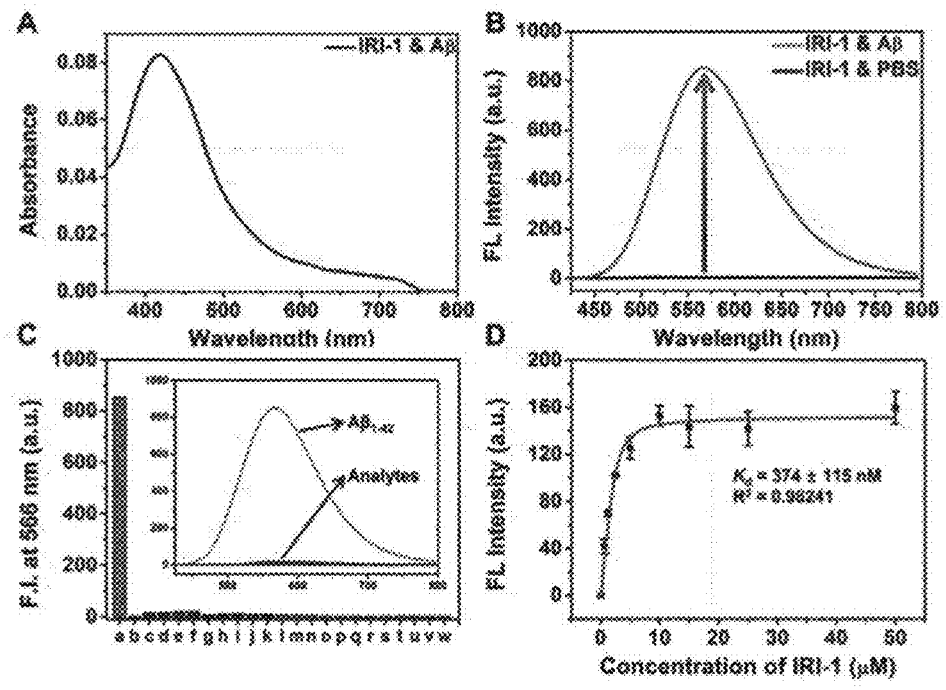
[Fig. 2]
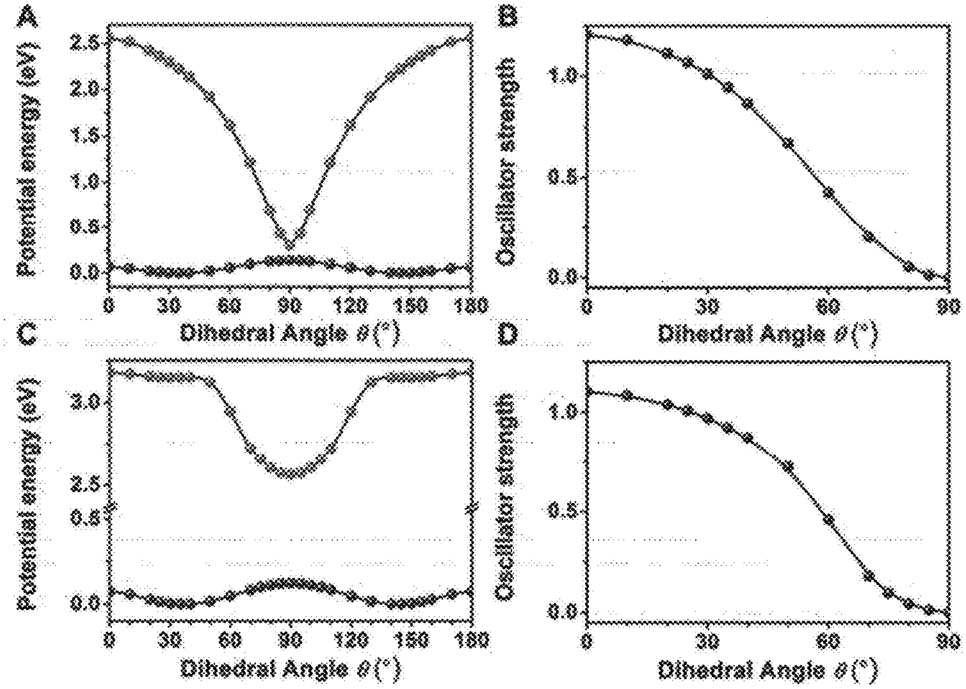

[Fig. 3]
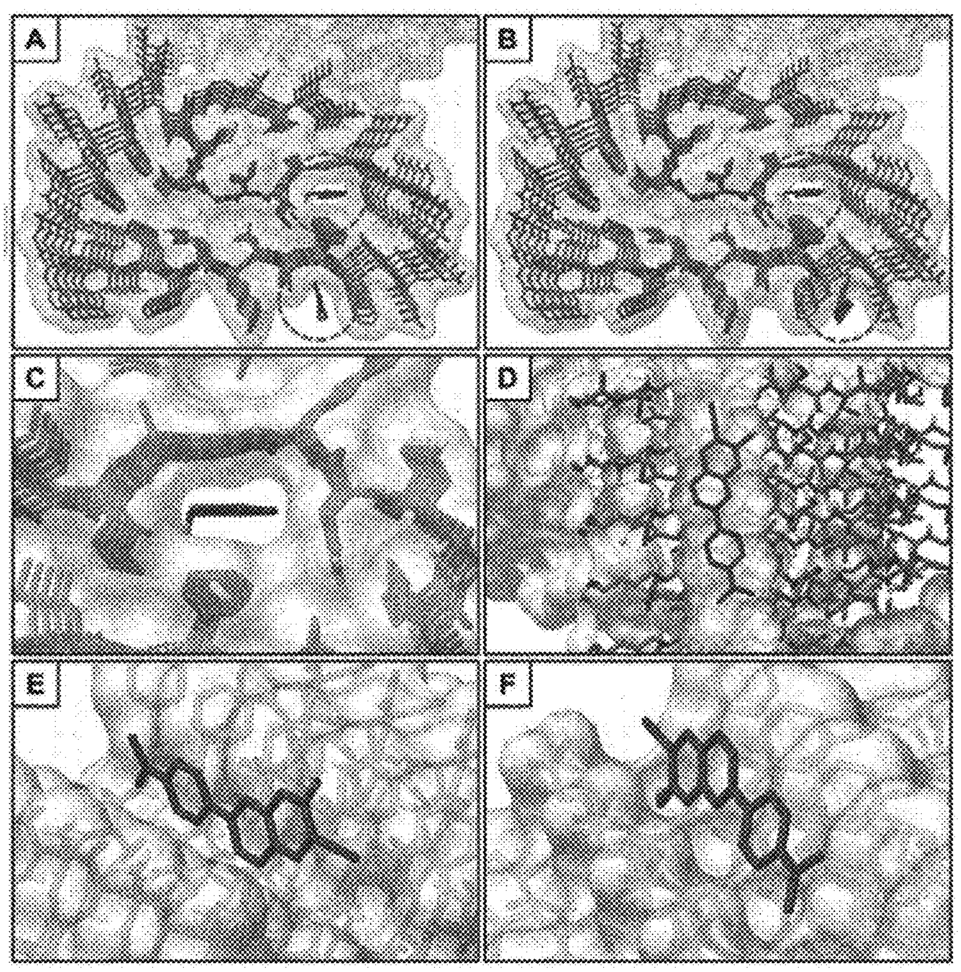
[Fig. 4]
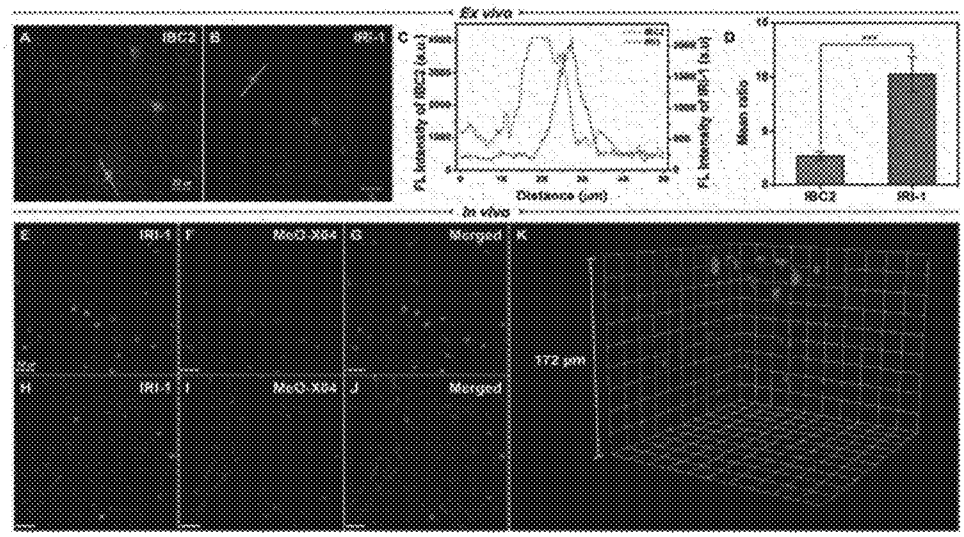

[Fig. 5]
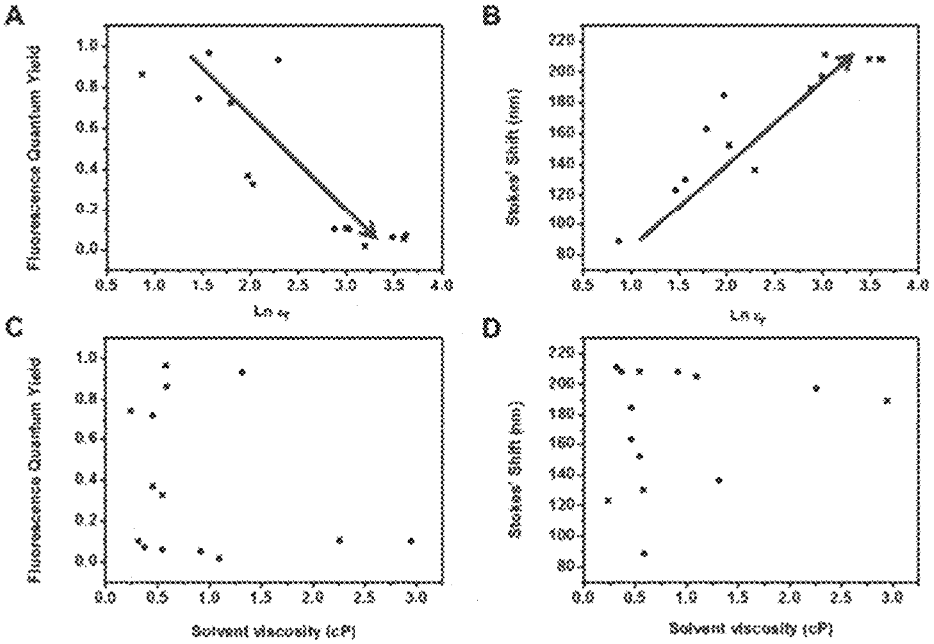
[Fig. 6]
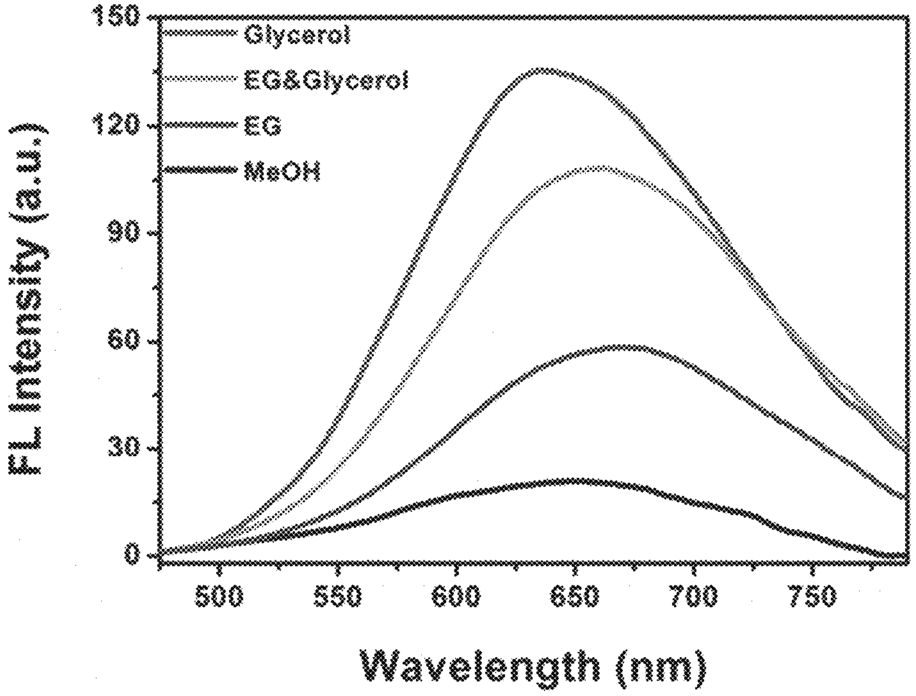

[Fig. 7]
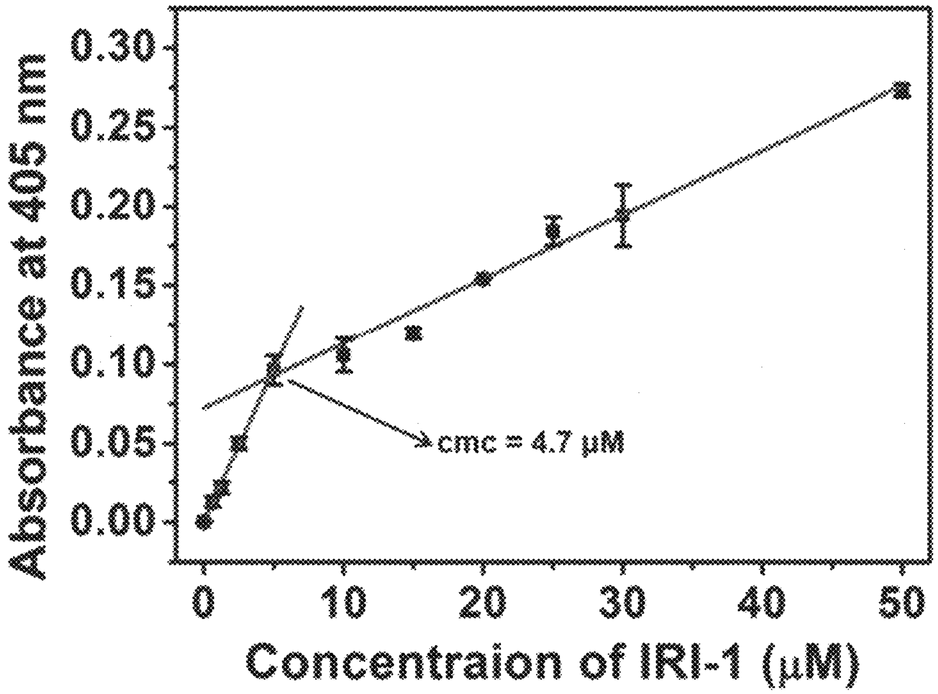

[Fig. 8]
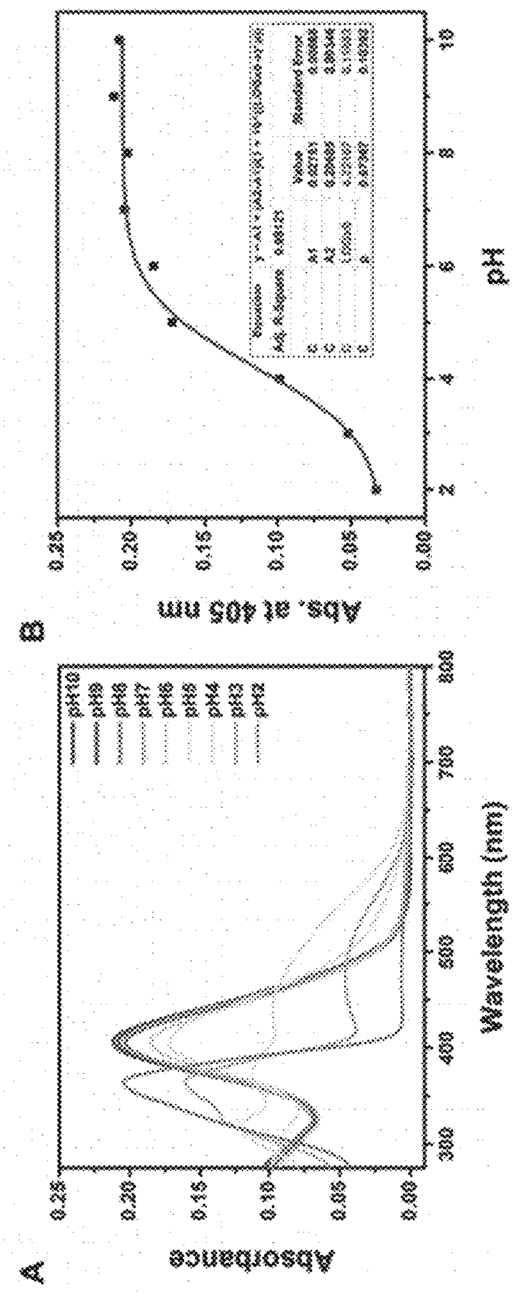

[Fig. 9]
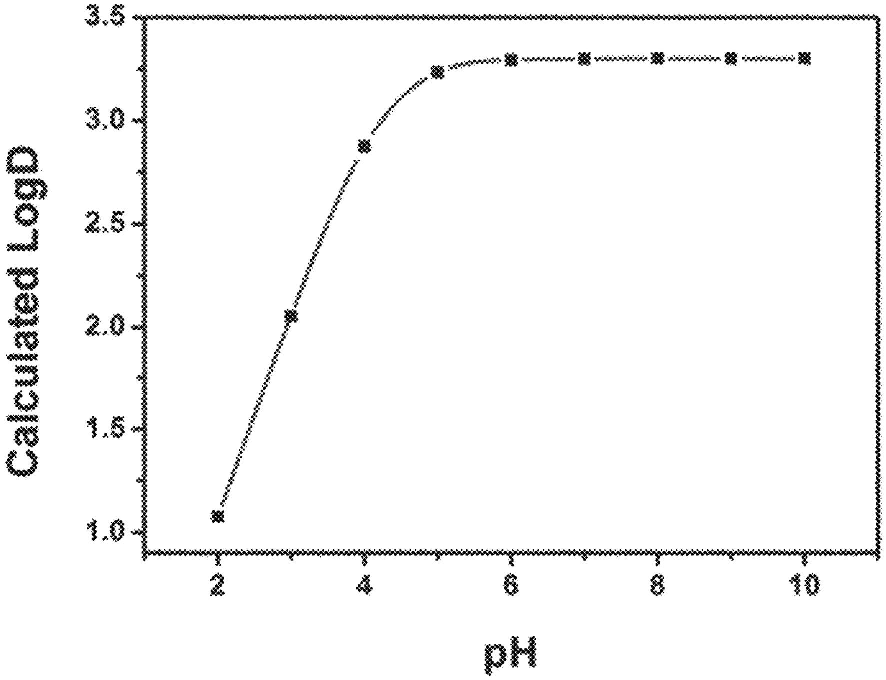

[Fig. 10]
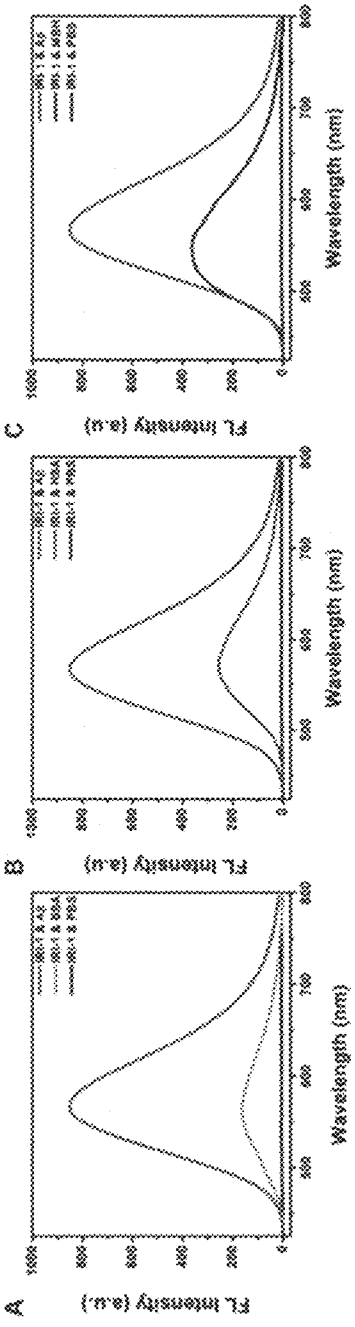

[Fig. 11]
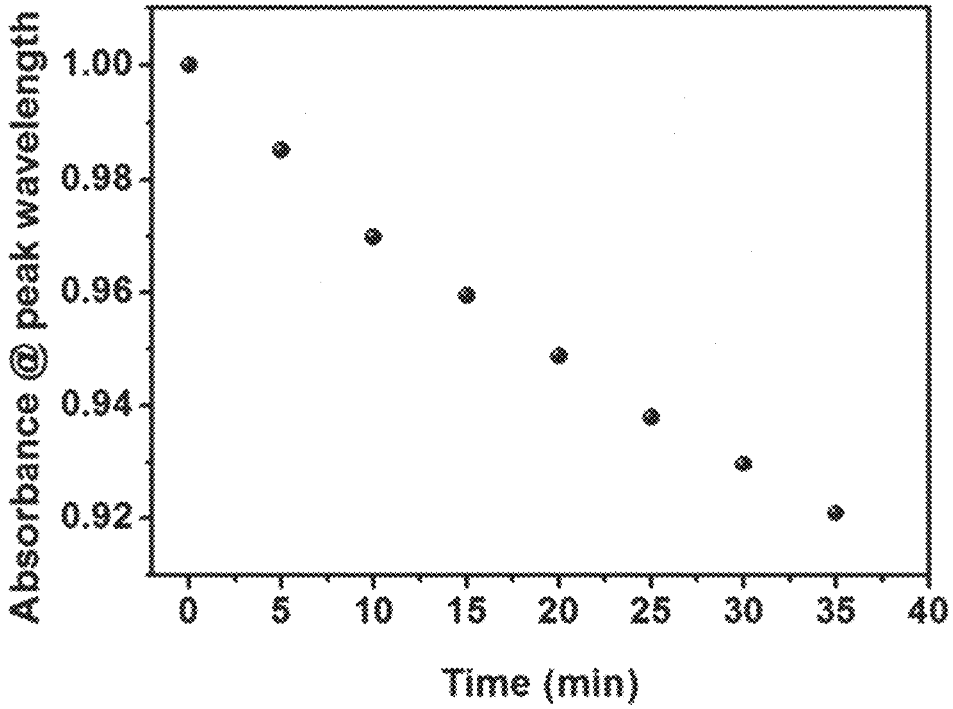
[Fig. 12]
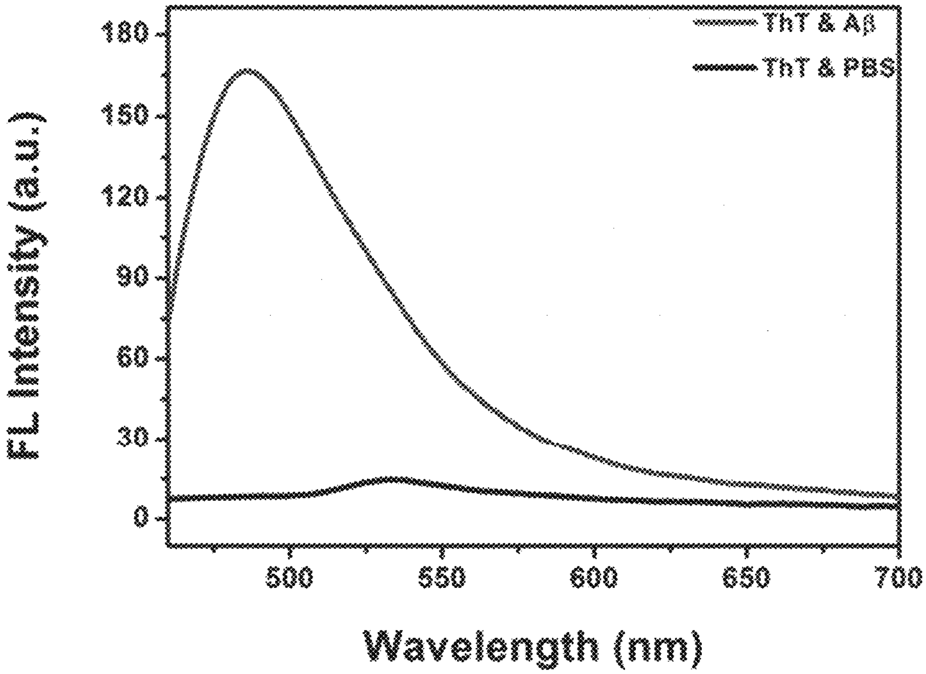

[Fig. 13]
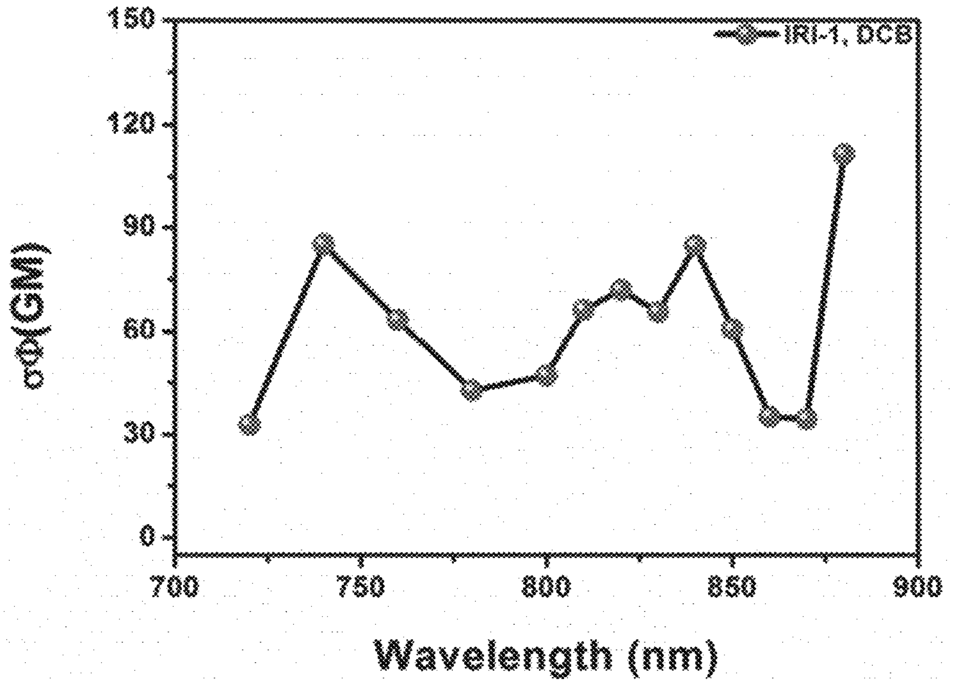
[Fig. 14]
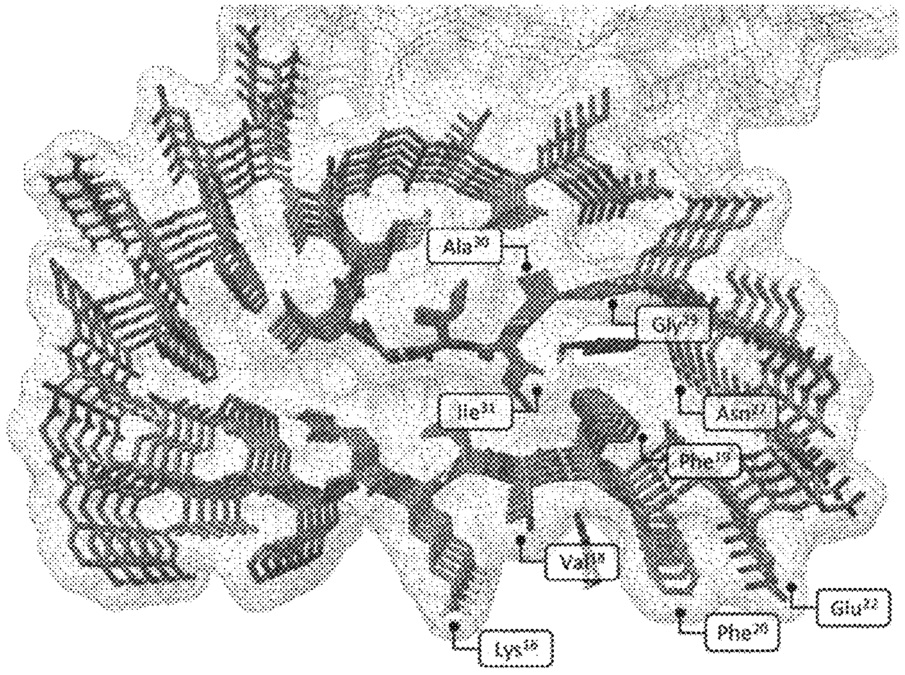

[Fig. 15]
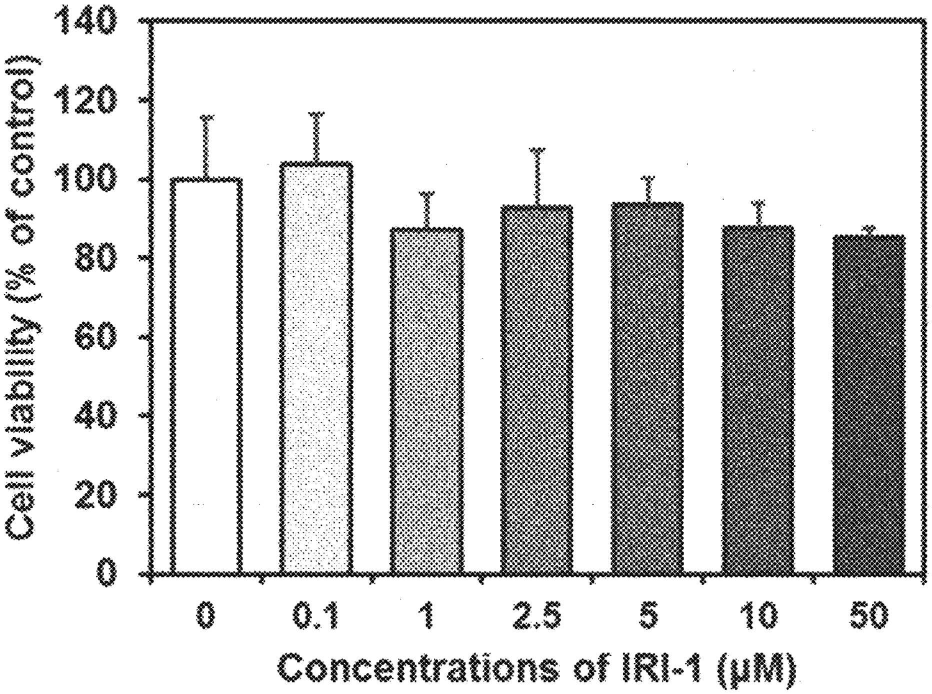
[Fig. 16]
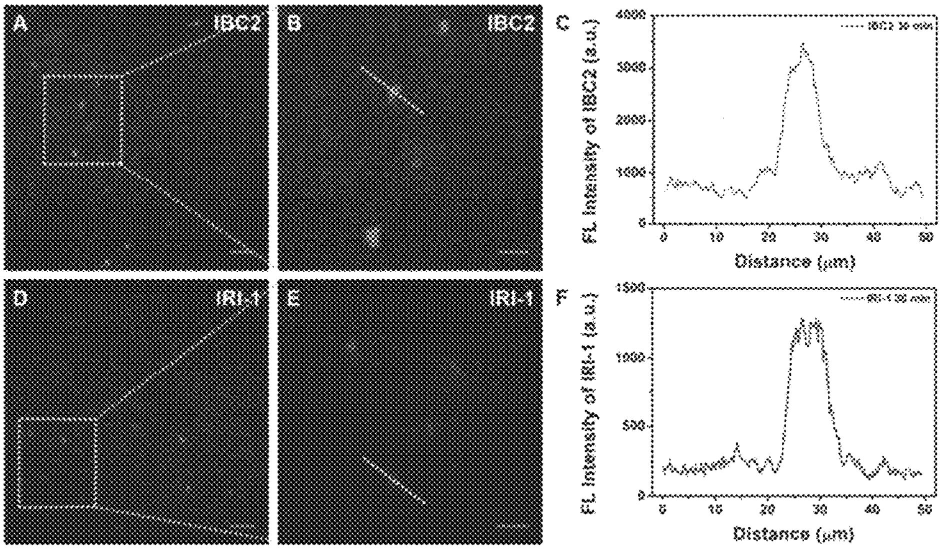

[Fig. 17]
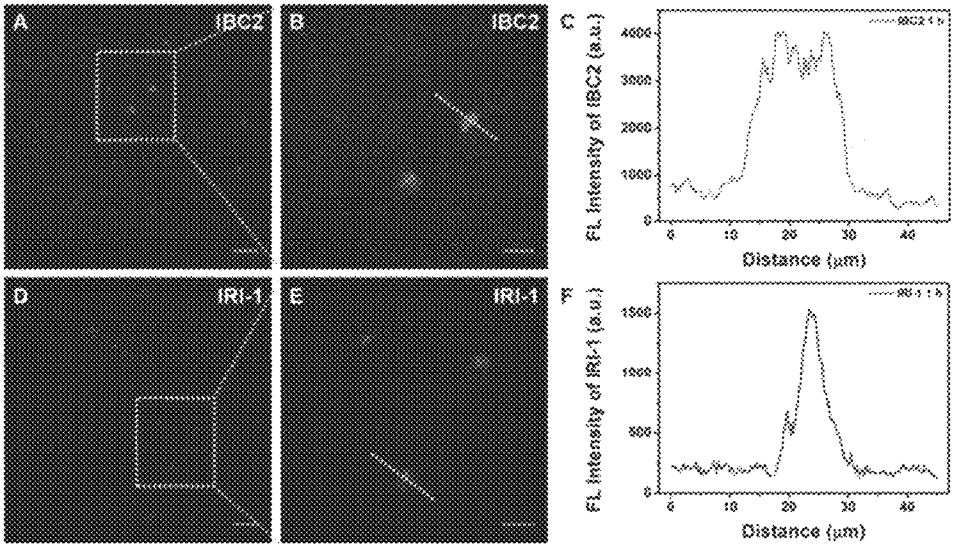
[Fig. 18]
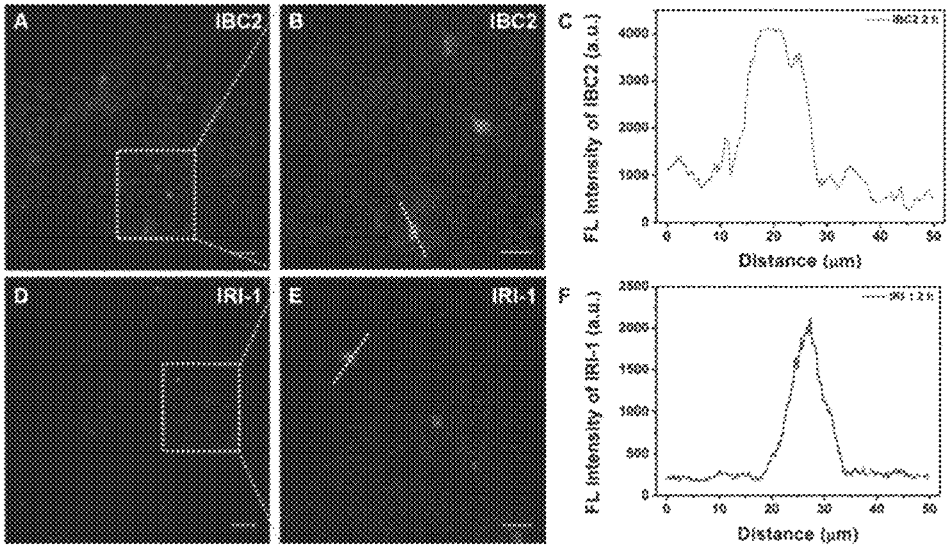

[Fig. 19]
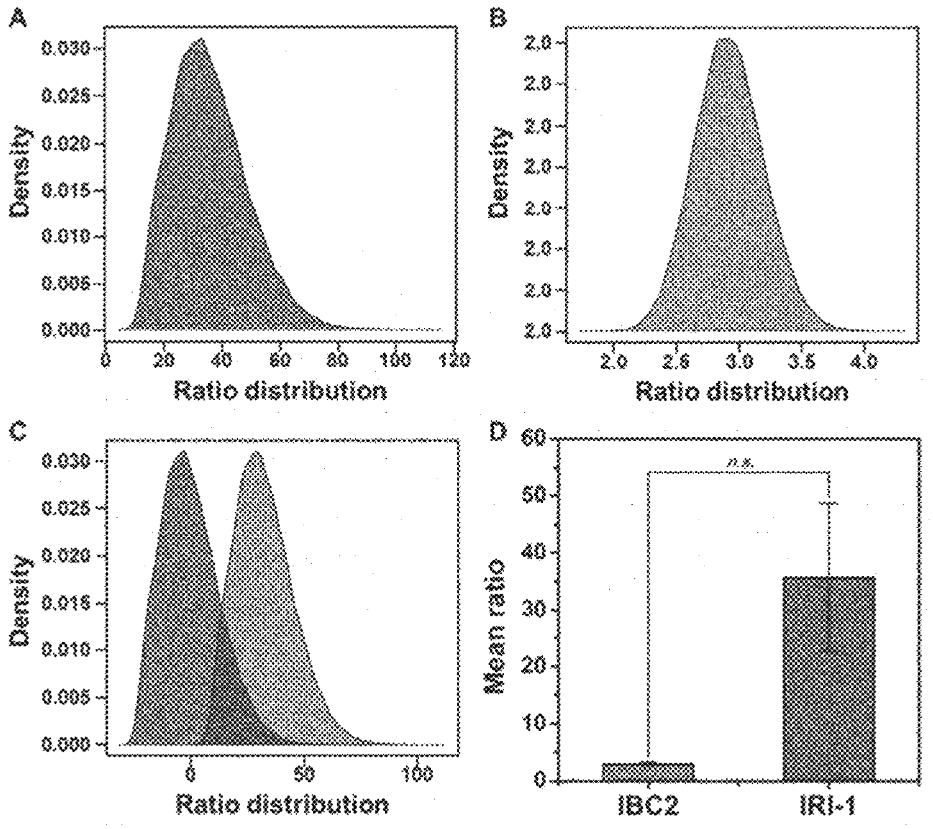

[Fig. 20]
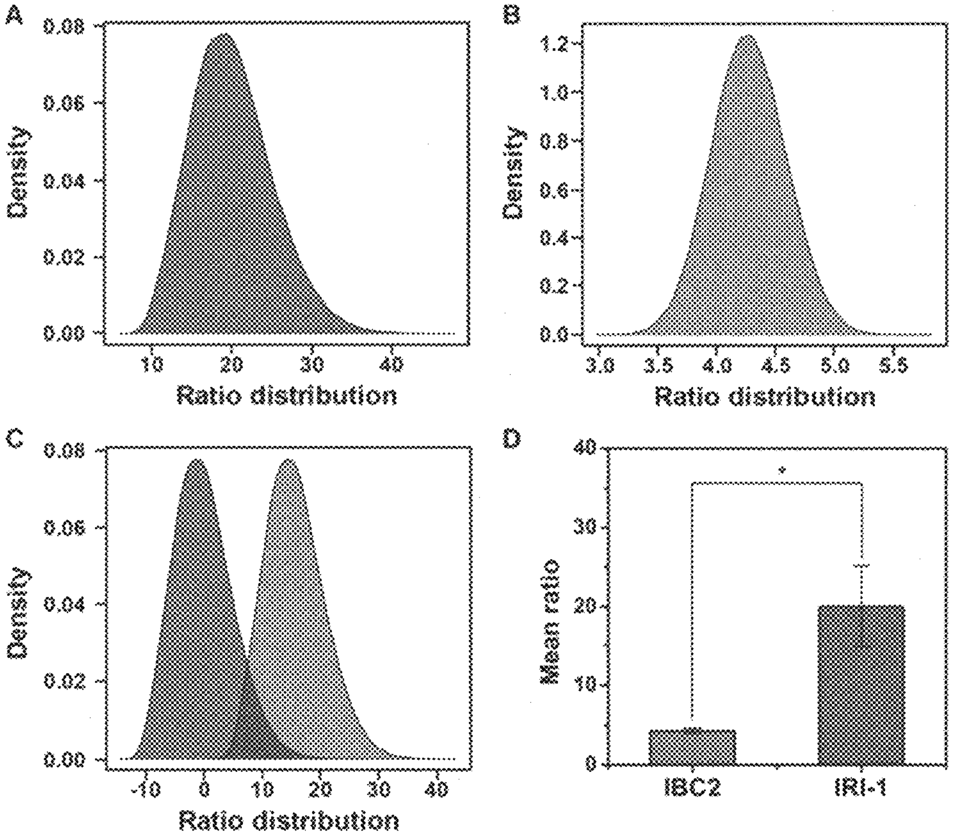

[Fig. 21]
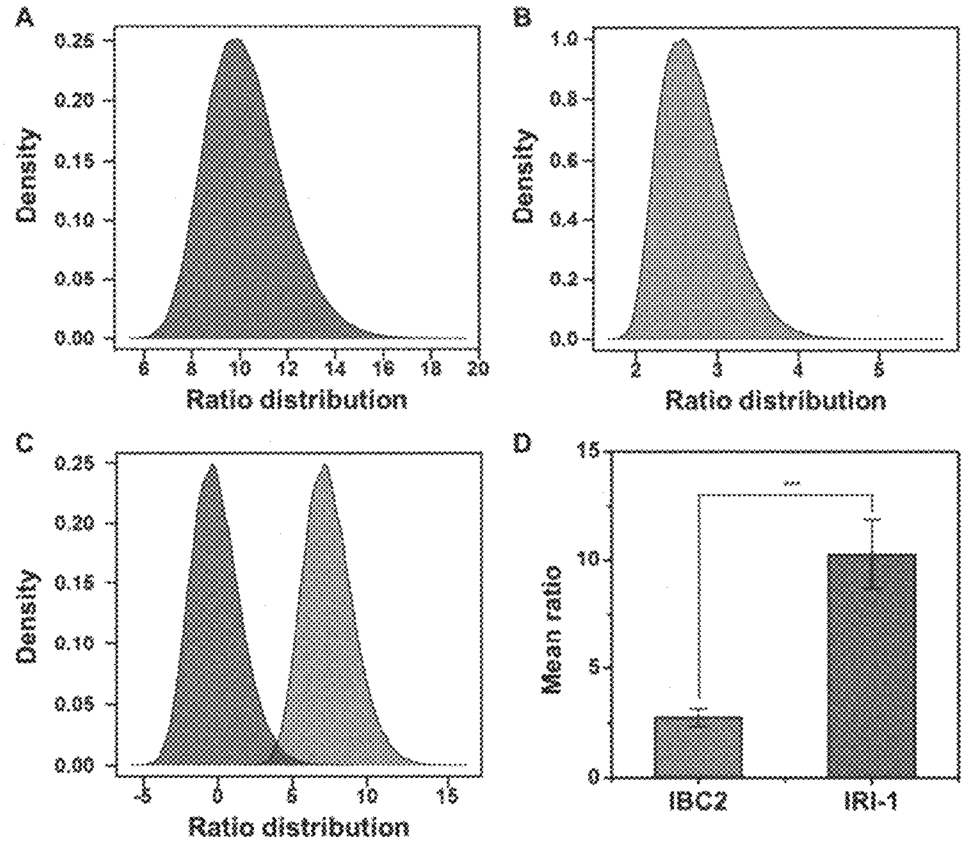

[Fig. 22]
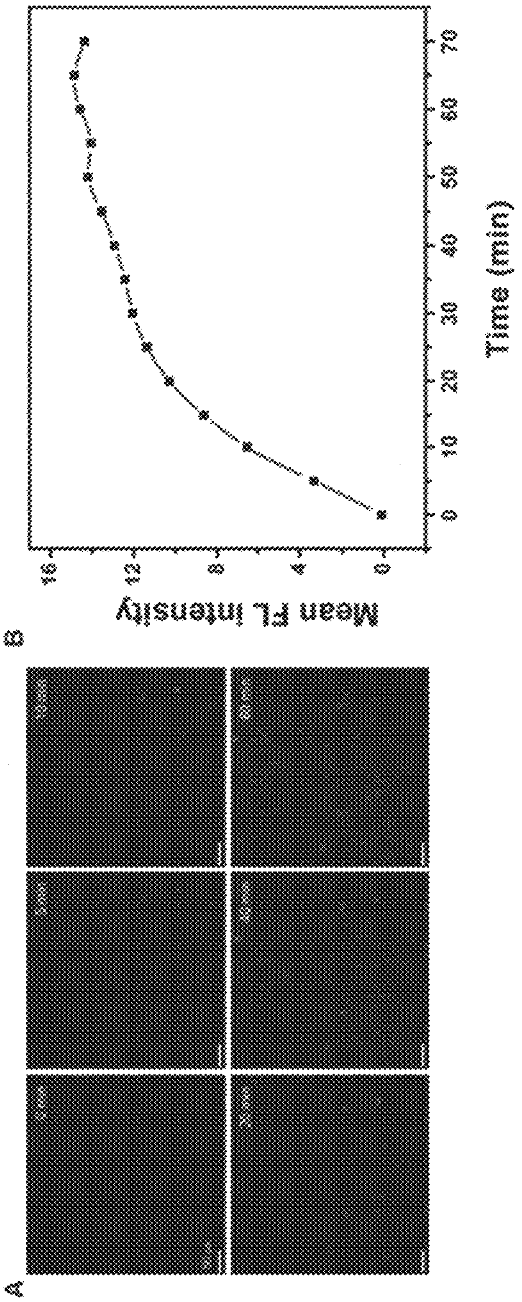

[Fig. 23]
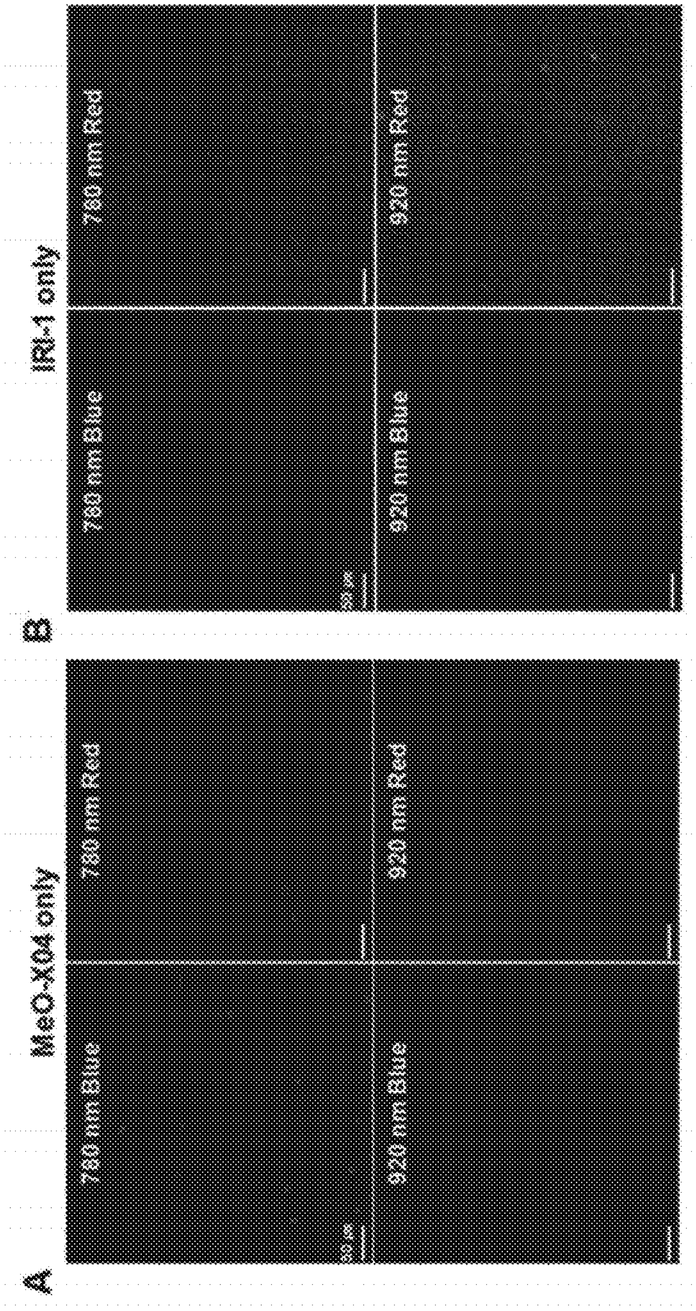

[Fig. 24]
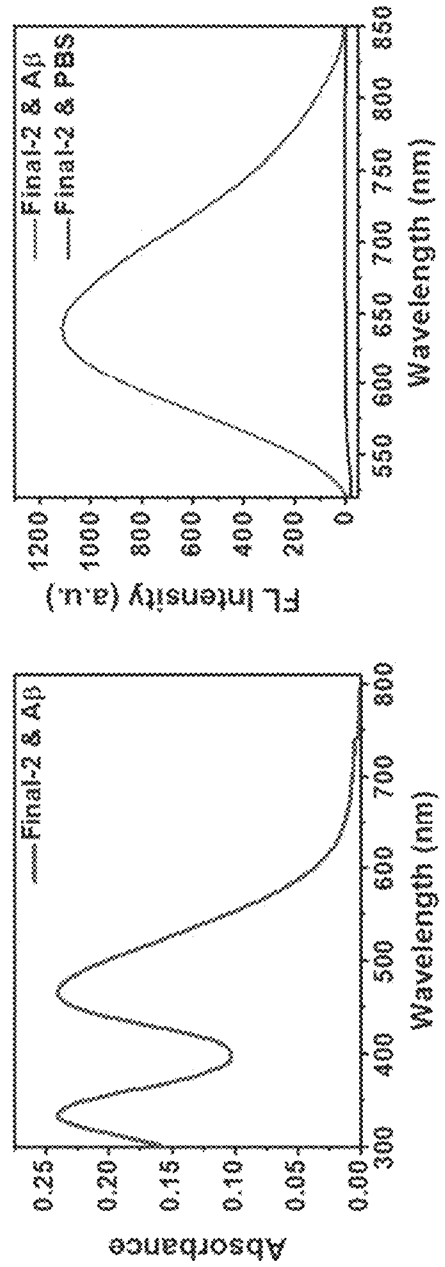

[Fig. 25]
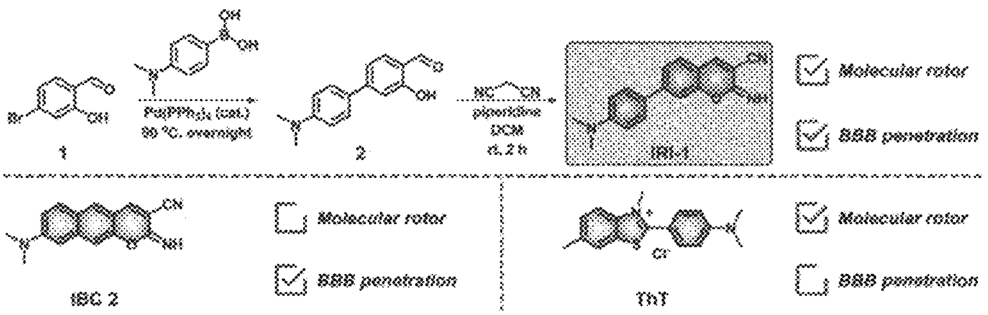
[Fig. 26]
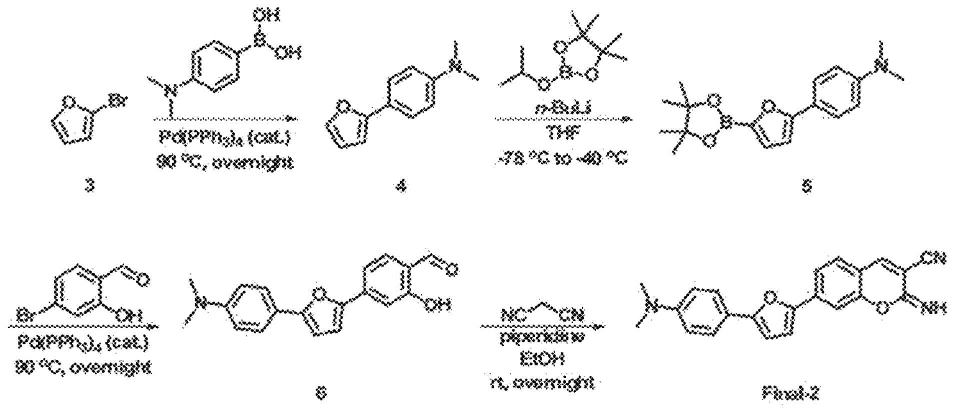

TWO-PHOTON FLUORESCENT PROBE COMPOUND SELECTIVE FOR AMYLOID BETA PLAQUES AND METHOD FOR IMAGING AMYLOID BETA PLAQUES USING SAME

CROSS REFERENCE TO RELATED APPLICATIONS

This application is a National Stage of International Application No. PCT/KR2021/001002 filed Jan. 26, 2021, claiming priority based on Korean Patent Application No. 10-2020-0023888 filed Feb. 26, 2020.

TECHNICAL FIELD

The present invention relates to a two-photon fluorescent probe compound selective for amyloid beta plaques and a method for imaging amyloid beta plaques using the same.

BACKGROUND ART

The aggregation of amyloid beta (AB) proteins in senile plaques is a critical biomarker for Alzheimer's disease and the postmortem detection of proteinaceous deposits through fluorescence response is one of the most powerful diagnostic tools for Alzheimer's disease. In animal models of Alzheimer's disease, fluorescence imaging can be employed to follow the progression of the disease, and among the different imaging methods, two-photon microscopy (TPM) has emerged as one of the most effective.

In this connection, several near-infrared-emissive two-photon probes with high selectivity for Aβ proteins have been reported (Non-Patent Documents 1 to 3), but they suffer from reduced fluorescence due to high background fluorescence or have poor blood-brain barrier (BBB) penetrability despite their advantage of large two-photon cross section.

(Non-Patent Document 1) M. Hintersteiner et al, Nat. Biotechnol., 2005, 23, 577
(Non-Patent Document 2) W. E. Klunk et al, Ann. Neurol., 2004, 55, 306
(Non-Patent Document 3) F. Helmchen et al, Nat. Methods, 2005, 2, 932; W. R. Zipfel et al, Nat. Biotechnol., 2003, 21, 1369-1377

DETAILED DESCRIPTION OF THE INVENTION

Problems to be Solved by the Invention

The present invention has been made in an effort to solve the above-described problems and intends to provide a novel intramolecular rotation-enabled two-photon fluorescent probe compound in which a twisted intramolecular charge state (TICT)-based fluorescence quenching pathway is introduced, which results in a remarkable fluorescence increase specifically in response to Aβ proteins, while maintaining an excellent two-photon cross-section, and which has a high signal-to-noise ratio and excellent BBB penetrability, and a method for imaging amyloid beta plaques using the two-photon fluorescent probe compound.

Means for Solving the Problems

One aspect of the present invention provides a two-photon fluorescent probe compound represented by Formula 1:

[Formula 1]

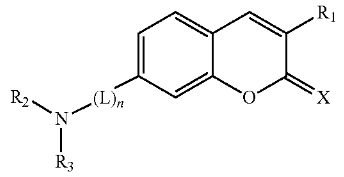

The structure of Formula 1 is described below and the substituents in Formula 1 are as defined below.

The present invention also provides a composition for detecting amyloid beta including the two-photon fluorescent probe compound represented by Formula 1.

The present invention also provides a method for imaging amyloid beta plaques, including: injecting the two-photon fluorescent probe compound represented by Formula 1 into a sample isolated from a living body; allowing the two-photon fluorescent probe compound to bind to amyloid beta plaques in the sample; irradiating an excitation source onto the sample; and monitoring fluorescence generated from the two-photon fluorescent probe compound with a two-photon microscope.

Effects of the Invention

The two-photon fluorescent probe compound of the present invention exhibits minimal background fluorescence while maintaining an excellent two-photon fluorescence cross-section, achieving a high signal-to-noise ratio. Thus, the two-photon fluorescent probe compound of the present invention shows efficient BBB penetration and high selectivity and sensitivity for Aβ plaques, enabling effective imaging of Aβ plaques. Therefore, the two-photon fluorescent probe compound of the present invention could find applications in the field of neurodegenerative research, including the early diagnosis and treatment of Alzheimer's disease.

BRIEF DESCRIPTION OF THE DRAWINGS

FIG. 1 shows the absorbance and fluorescence data of the compound (iminocoumarin 1, IRI-1) (10 μM) represented by Formula 2. (A) Absorption spectra of IRI-1 in the presence of Aβ fibrils (20 μM). (B) Fluorescence spectra of IRI-1 in PBS and Aβ fibrils (20 μM) (slit 3/5). (C) Fluorescence response assays ($\lambda_{em}$: 566 nm) for IRI-1 and various potential interferents: a: Aβ fibrils (20 μM), b-k: metal ions (20 μM, b: $Al^{3+}$, c: $Fe^{3+}$, d: $Fe^{2+}$, e: $Ca^{2+}$, f: $Cu^{2+}$, g: $Zn^{2+}$, h: $Ni^{2+}$, i: $Mg^{2+}$, j: $Na^{+}$, k: $K^{+}$), 1-s: amino acids (20 μM, 1: Lys, m: Arg, n: Asp, o: Glu, p: His, q: Trp, r: Tyr, s: Phe), and t-w: thiols (20 μM, t: DTT, u: Hcy, v: GSH, w: Cys), in PBS, slit 3/5. (D) Saturation binding curve of Aβ fibrils (10 μM) as a function of [IRI-1] (0-50 μM) in PBS (error bars represent SD (n=3), slit 3/3).

FIG. 2 shows potential energy surface and oscillator strengths for the S1→S0 transitions as a function of the dihedral angle between the aromatic rings, using an equilibrium-state-specific PCM model at the ωB97XD/N07D//B3LYP/N07D level of theory ((A,B) Solvent-water. (C,D) solvent=cyclohexane).

FIG. 3 shows the top view of an $A\beta_{1-42}$ protofibril (with a partial structure of the second protofibril). (A) Protein-ligand interactions on the $Val^{18}$, $Phe^{20}$ surface and the internal tunnel. (B) Protein-ligand interactions on the $Phe^{20}$, $Glu^{22}$ surface and the internal tunnel. (C) Top view of IRI-1 encapsulated by the $A\beta_{1-42}$ $Phe^{19}$, $Asn^{27}$, $Gly^{29}$, $Ile^{31}$ surface. (D) Clipped view of IRI-1 within the tunnel. (E) $Lys^{16}$, $Val^{18}$, $Phe^{20}$ groove (cf. 3A). (F) $Phe^{20}$, $Glu^{22}$ groove (cf. 3B).

FIG. 4 shows ex vivo and in vivo TPM imaging of 5×FAD-Tg mouse brains. (A-D) Ex vivo imaging with IRI-1 (A) and IBC-2 (B). (C) The fluorescence profiles through a single Aβ plaque with IBC-2 and IRI-1 as indicated in (A) and (B), respectively. (D) Mean TPM fluorescence signal-to-background ratios for IRI-1- and IBC-2-treated brain tissues (n=15). The fluorescence ($\lambda_{em}$=580-779 nm) was monitored by TPM at an excitation wavelength of 850 nm with laser power approximately 50 mW at the focal point, at an image depth of approximately 75 mm (Scale bars=25 mm, Error bars indicate SD. *** $p<0.005$. (E-K) In vivo TPM imaging of the distribution of Aβ plaques co-stained with IRI-1 (E) and MeO—X04 (F) in the frontal cortex of transgenic mice (5×FAD-Tg, 10-12-month-old). (G) Merged image. (H-J) Cerebral amyloid angiopathy (CAA) near the blood vessel walls. Fluorescence images were monitored under excitation at 920 nm (E, H) and 780 nm (F, I) (Scale bars: 25 μm). (K) 3D in vivo imaging of IRI-1-stained Aβ plaques after intraperitoneal administration (5 mg kg-1).

FIG. 5 shows the photophysical property of IRI-1. (A) and (B) show the solvent fluorescence quantum yield and the Stokes' shift with the natural logarithm of the solvent dielectric constant, respectively. (C) and (D) shows the solvent fluorescence quantum yield and the Stokes' shift with the solvent viscosity (Solvents: acetone, acetonitrile, 1-butanol, chloroform, 1,2-dichlorobenzene, diethyl ether, N,N-dimethylformamide, ethanol, ethyl acetate, ethylene glycol, methanol, 1-propanol, tetrahydrofuran, and toluene). $\lambda_{ex}$=405 nm. Slit width 3/5. The fluorescence quantum yield was determined relative to 4-(dicyanomethylene)-2-methyl-6-(4-dimethylaminostyryl)-4H-pyran in acetonitrile.

FIG. 6 shows fluorescence spectra of IRI-1 in solvents with increasing viscosity. (IRI-1:10 μM, $\lambda_{ex}$: 405 nm, slit width: 3/5, EG: ethylene glycol).

FIG. 7 shows PBS solubility, specifically absorbance values of IRI-1 at 405 nm at various concentrations in PBS. A shift from monomers to soluble aggregates was observed for IRI-1 concentrations exceeding 4.7 μM. Error bars indicate standard deviation, n=3.

FIG. 8 shows pH-dependent absorbance changes. (A) Absorbance spectra of IRI-1 at various pH levels. (B) The pH-dependent absorbance at 405 nm, with non-linear $pK_a$ fitting.

FIG. 9 shows pH-dependent calculated Log D values. The Log D was calculated using the general equation for bases: Log D=Log P−Log $[1+10^{(pKa-pH)}]$, with $pk_a$=4.22 and Log P=3.30.

FIG. 10 shows fluorescence spectra of IRI-1 in PBS (10 mM, pH=7.4, containing 2% DMF), (A) BSA (20 μM), (B) HSA (20 μM) and (C) Mouse brain homogenates.

FIG. 11 shows photostability of IRI-1 in dimethylformamide (DMF).

FIG. 12 shows fluorescence spectra of ThT in PBS (10 mM, pH=7.4, containing 2% DMF) and Aβ fibrils (20 μM) (Excited at 450 nm).

FIG. 13 shows two-photon action spectra of IRI-1 (10 μM) acquired in 1,2-dichlorobenzene (DCB).

FIG. 14 shows the location of key residues in the Cryo-EM structure.

FIG. 15 shows the results of cytotoxicity measurement. Human neuroblast SH-SY5Y cells were treated with various concentrations of IRI-1 for 24 h. The cells were washed with PBS three times and the cytotoxicity was determined using an MTT assay (n=3).

FIG. 16 shows ex vivo TPM imaging of mice brain slices after 30 min incubation. (A) Images obtained using IBC 2. (B) Zoomed images as indicated in panel A. (C) Extracted fluorescence intensities along the trace indicated in panel B. (D) Images obtained using IRI-1. (E) Zoomed images as indicated in panel D. (F) Extracted fluorescence intensities along the trace indicated in panel E. Scale bars in panels A and D: 50 μm. Scale bars in panels B and E: 25 μm.

FIG. 17 shows ex vivo TPM imaging of mice brain slices after 1 h incubation. (A) Images obtained using IBC 2. (B) Zoomed images as indicated in panel A. (C) Extracted fluorescence intensities along the trace indicated in panel B. (D) Images obtained using IRI-1. (E) Zoomed images as indicated in panel D. (F) Extracted fluorescence intensities along the trace indicated in panel E. Scale bars in panels A and D: 50 μm. Scale bars in panels B and E: 25 μm.

FIG. 18 shows ex vivo TPM imaging of mice brain slices after 2 h incubation. (A) Images obtained using IBC 2. (B) Zoomed images as indicated in panel A. (C) Extracted fluorescence intensities along the trace indicated in panel B. (D) Images obtained using IRI-1. (E) Zoomed images as indicated in panel D. (F) Extracted fluorescence intensities along the trace indicated in panel E. Scale bars in panels A and D: 50 μm. Scale bars in panels B and E: 25 μm.

FIG. 19 shows the results of statistical analysis (bootstrap) of the signal to background ratios after 30 min incubation. (A) Probability density of the distribution of the IRI-1 signal to background ratio. (B) Probability density of the distribution of the IBC 2 signal to background ratio. (C) Difference of the IRI-1 and IBC 2 ratios as observed and under the $H_0$ hypothesis, showing the degree of distribution overlap (proportional to the p-value). (D) Mean ratio and standard deviation of the IRI-1 and IBC 2 signal to background ratios indicating the degree of statistical significance (n.s.: not significant).

FIG. 20 shows the results of statistical analysis (bootstrap) of the signal to background ratios after 1 h incubation. (A) Probability density of the distribution of the IRI-1 signal to background ratio. (B) Probability density of the distribution of the IBC 2 signal to background ratio. (C) Difference of the IRI-1 and IBC 2 ratios as observed and under the $H_0$ hypothesis, showing the degree of distribution overlap (proportional to the p-value). (D) Mean ratio and standard deviation of the IRI-1 and IBC 2 signal to background ratios indicating the degree of statistical significance. (n.s.: not significant, * $p<0.05$).

FIG. 21 shows the results of statistical analysis (bootstrap) of the signal to background ratios after 2 h incubation. (A) Probability density of the distribution of the IRI-1 signal to background ratio. (B) Probability density of the distribution of the IBC 2 signal to background ratio. (C) Difference of the IRI-1 and IBC 2 ratios as observed and under the $H_0$ hypothesis, showing the degree of distribution overlap (proportional to the p-value). (D) Mean ratio and standard deviation of the IRI-1 and IBC 2 signal to background ratios indicating the degree of statistical significance. (***: $p<0.005$).

FIG. 22 shows time-dependent TPM intensity in vivo. The fluorescence intensity was determined post intraperitoneal injection of IRI-1 using excitation at 920 nm and the emission was recorded in the red channel (555-610 nm). (A) Selected images. (B) Time-dependent average fluorescence intensity.

FIG. 23 shows in vivo imaging of Aβ plaques with MeO—X04 or IRI-1. (A) MeO—X04 TPM images using the excitation wavelengths as indicated in the figure and using the blue (485-490 nm) or red (555-610 nm) emission window, as indicated in the figure. (B) IRI-1 TPM images using the excitation wavelengths as indicated in the figure and using the blue (485-490 nm) or red (555-610 nm) emission window, as indicated in the figure. The dyes were administered intraperitoneally (5 mg kg-1), and the laser power was approximately 30 mW at the focal point. Scale bar is 50 μm.

FIG. 24 shows absorbance and fluorescence spectra of the compound (Final-2) represented by Formula 8 in PBS buffer (pH 7.4, containing 2% DMF) and in the presence of Aβ fibrils (20 μM) in PBS buffer (pH 7.4).

FIG. 25 shows a synthetic route to the compound (IRI-1) represented by Formula 2 according to the present invention.

FIG. 26 shows a synthetic route to the compound (Final-2) represented by Formula 8 according to the present invention.

BEST MODE FOR CARRYING OUT THE INVENTION

Unless otherwise defined, all technical and scientific terms used herein have the same meaning as commonly understood by one of ordinary skill in the art to which this invention belongs. In general, the nomenclature used herein is well known and commonly employed in the art.

The present invention is directed to a novel two-photon fluorescent probe compound selective for amyloid beta plaques.

The two-photon fluorescent probe compound of the present invention is represented by Formula 1:

[Formula 1]

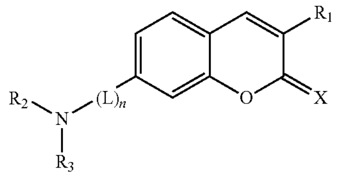

wherein X is selected from O and NR, R is selected from hydrogen, deuterium and $C_1$-$C_7$ alkyl, $R_1$ is cyano (CN) or

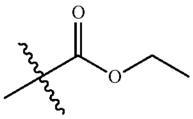

,

L is aryl or heteroaryl, n is 1 or 2, and $R_2$ and $R_3$ are the same as or different from each other and are each independently selected from hydrogen, deuterium, and $C_1$-$C_7$ alkyl, with the proviso that $R_2$ and $R_3$ are optionally bonded together to form a ring or combined with L to form a ring.

According to the present invention, L may be

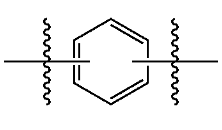

or

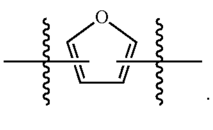

.

According to the present invention, the two-photon fluorescent probe compound represented by Formula 1 may be selected from the compounds represented by Formulae 2 to 13:

[Formula 2]

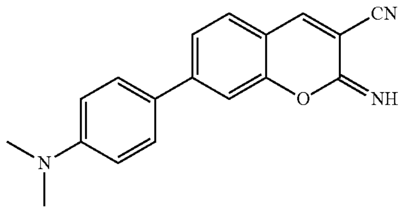

[Formula 3]

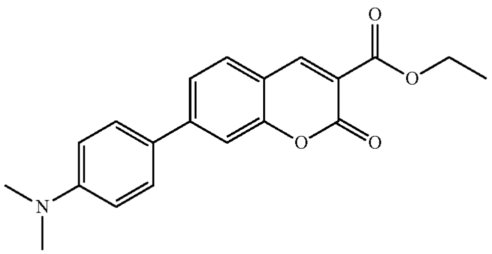

[Formula 4]

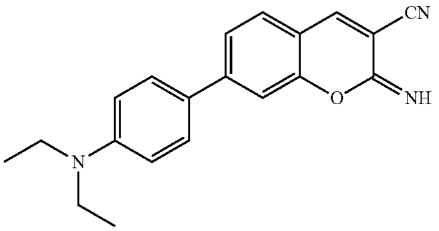

[Formula 5]

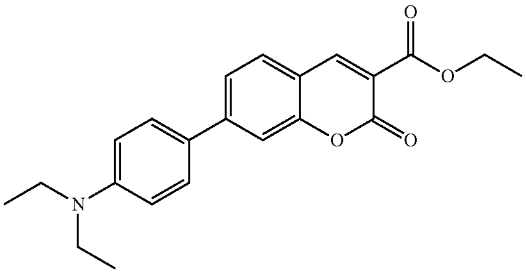

[Formula 6]

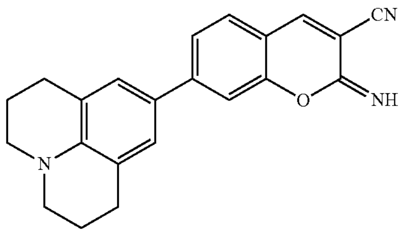

-continued

[Formula 7]

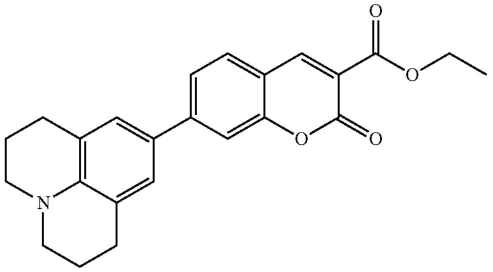

[Formula 8]

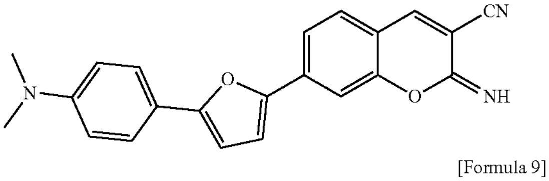

[Formula 9]

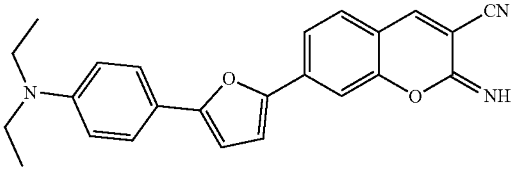

[Formula 10]

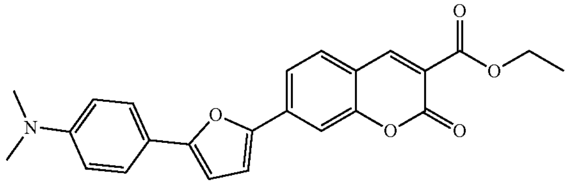

[Formula 11]

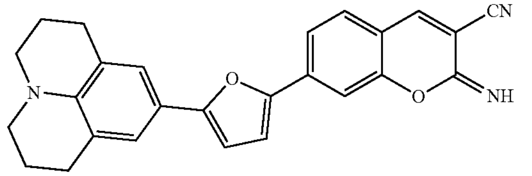

[Formula 12]

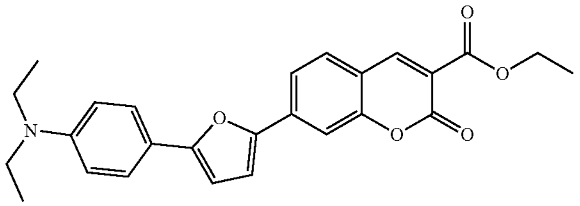

[Formula 13]

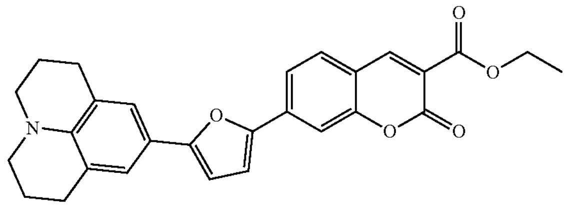

The two-photon fluorescent probe compound of the present invention may specifically bind to amyloid beta plaques.

The present invention also provides a composition for detecting amyloid beta including the two-photon fluorescent probe compound represented by Formula 1.

The present invention also provides a method for imaging amyloid beta plaques, including: injecting the two-photon fluorescent probe compound represented by Formula 1 into a sample isolated from a living body; allowing the two-photon fluorescent probe compound to bind to amyloid beta plaques in the sample; irradiating an excitation source onto the sample; and monitoring fluorescence generated from the two-photon fluorescent probe compound with a two-photon microscope.

The sample isolated from a living body may be a cell or tissue sample.

The two-photon fluorescent probe compound of the present invention exhibits minimal background fluorescence while maintaining an excellent two-photon fluorescence cross-section, achieving a high signal-to-noise ratio. Thus, the two-photon fluorescent probe compound of the present invention shows efficient BBB penetration and high selectivity and sensitivity for Aβ plaques, enabling effective imaging of Aβ plaques. Therefore, the two-photon fluorescent probe compound of the present invention could find applications in the field of neurodegenerative research, including the early diagnosis and treatment of Alzheimer's disease.

MODE FOR CARRYING OUT THE INVENTION

Examples

The present invention will be explained in more detail with reference to the following examples. It will be evident to those skilled in the art that these examples are merely for illustrative purposes and are not to be construed as limiting the scope of the present invention. Therefore, the true scope of the present invention is defined by the appended claims and their equivalents.

Experimental Procedures

Materials, Methods and Instruments

All reagents and solvents were obtained from commercial suppliers (TCI, Thermofisher, Merck, Samchun) and were used without further purification. Anhydrous THF was distilled over Na/benzophenone. $A\beta_{1-42}$ peptides were purchased from GenicBio Limited (Shanghai, China). NMR spectra were obtained on a 500 MHz Bruker NMR spectrometer. UV/Vis spectra were recorded on a Jasco V-750 spectrometer, and fluorescence spectra were obtained using a Shimadzu RF-5301PC spectrofluorometer. Fluorescence spectra were corrected using correction files constructed according to a literature procedure (J. A. Gardecki, M. Maronceli, Apl. Spectrosc. 198, 52, 179-189). Mass spectroscopy (ESI-MS) was performed on a Shimadzu LCMS-2020 mass spectrometer system.

Quantum Yield and Determination of Emission and Fluorescence Wavelength Maxima

To prevent the inner filter effect, data were recorded with the absorbance lower than 0.1 at wavelengths longer or equal to the excitation wavelength using HPLC grade solvents. The quantum yields of IRI-1 were recorded versus 4-(dicyanomethylene)-2-methyl-6-(4-dimethylaminostyryl)-4H-pyran in acetonitrile. ($\Phi_{F1}$=0.6) (J. Bourson, B. Valeur, J. Phys. Chem. 1989, 93, 3871-3876).

Spectroscopy in Solvents

The emission spectra of IRI-1 (10 μM) in the media of $CH_3OH$, ethylene glycol, ethylene glycol and glycerol (1:1 v/v) and glycerol at 37° C. were recorded on a Shimadzu RF-5301PC spectrofluorometer. The IRI-1 stock solution was prepared in DMF and all solutions contain a final concentration of 2% DMF.

Solubility of IRI-1

The absorbance of IRI-1 at different concentrations in the 0-50 μM range was recorded at 405 nm in a PBS solution containing 2% DMSO. Deviation from linearity indicates the formation of aggregates.

Spectroscopy in the Presence of $A\beta_{1-42}$, Metal Ions, Amino Acids, Thiols, BSA, HSA and Brain Homogenates To measure spectra in the presence of analytes, stock solutions of ThT and IRI-1 were prepared in DMF and added to solutions of the analytes in PBS to finally obtain a solution containing 2% DMF. All emission spectra were obtained after 2 min stirring at 37° C. The excitation and emission slit widths were 3/5.

pH-Dependent Absorbance of IRI-1

The absorbance of IRI-1 (10 μM) was recorded in PBS (10 mM), with pH adjustment, to maintain a constant salt concentration.

Photostability

A solution of IRI-1 with an absorbance of 1.0 at the maximum absorbance wavelength was prepared in DMF. A 3100 K halogen lamp (Olympus LG-PS2; 12 V, 100 W) was used for irradiation and the absorbance was recorded at 5 min intervals for 35 min.

Two-Photon Cross-Sections

Two-photon cross-sections were determined using established procedures, (S. K. Le, W. J. Yang, J. J. Choi, C. H. Kim, S.-J. Jeon, B. R. Cho, Org. Let. 205, 7, 323-326) relative to Rhodamine 6G and Acedan.

Theoretical Calculations

The functional and polarizable continuum model screening of the S1←S0 and S1→S0 vertical transition energies, as well as the twisting angle dependent PES calculations were performed using the Gaussian 16 software package. The functionals included in the performance test were the B3LYP, CAM-B3LYP, ωB97X and ωB97XD functionals on their respective fully unrestrained optimized ground state geometries, and additionally the B3LYP-optimized geometry for the range separated functionals, using the 6-31G-derived N07D basis set. Excited state calculations were performed, with the implementation of a twisting angle of 35° between donor and acceptor moieties of IRI-1. Similar state calculations were performed similarly. Polarizable continuum models of acetonitrile were employed, using the default linear response method of the IEFPCM solvation model, as well as two state-specific approaches (M. Caricato et al., J. Chem. Phys. 206, 124, 124520; R. Improta et al., J. Chem. Phys. 206, 125, 054103). For PES calculations, a partially constrained geometry optimization of the probe was performed using the B3LYP functional at the N07D level of theory using the default linear response implementation of the IEFPCM solvation method of water and cyclohexane, for both the ground state and excited state, where the dihedral angle was set to the values indicated in the corresponding figures. The energy of each of the optimized conformations was recalculated at the ωB97XD/N07D level of theory, with state-specific corrections to the solvent reaction field. The S1→S0 oscillator strengths were obtained from these TDDFT calculation as well. Input file generation and molecular orbital visualizations were performed using Gabedit 2.5.0.

Docking Studies

The ground-state B3LYP-optimized structure of IRI-1 was used as the ligand for docking studies. The cryo-EM structure (PDB ID: 50QV) (L. Gremer et al., Science 2017, 358, 16-19) was prepared by removing either the $Glu^{22}$ or $Val^{18}$-facing conformation of $Phe^{20}$ and one entire protofibril was encompassed within the search area (38×50×32 Å) using AutoDock Vina (O. Trot, A. J. Olson, J. Comput. Chem. 2010, 31, 45-461) as the docking software. The identified docking sites were then recalculated using a smaller search area of (14×14×26 Å) for the tunnel and (14×20×26 Å) for the binding sites adjacent to $Phe^{20}$. The input for the docking calculations was prepared using AutoDockTools 4.2 (G. M. Moris et al., J. Comput. Chem. 209, 30, 2785-2791) and figures were generated using the Python Molecule Viewer 1.5.6 software package (M. F. Saner, J. Mol. Graphics Model., 199, 17, 57-61).

$A\beta_{1-42}$ Aggregation $A\beta_{1-42}$ protein was prepared following a literature procedure (J. Hatai, L. Motiei, D. Margulies, J. Am. Chem. Soc. 2017, 139, 2136-2139). Briefly, lyophilized $A\beta_{1-42}$ peptides were dissolved in 100% HFIP (1,1,1,3,3,3-hexafluoro-2-isopropanol) at a concentration of 2 mg $mL^{-1}$ and incubated at 25° C. for 2 h. After incubation, solution was removed under a gentle flow of argon. The peptide was dried using a lyophilizer for 40 h. Aβ (1 mg) was resuspended in aqueous NaOH (0.5 mL, 2 mM) and sonicated at 0° C. for 10 min. HFIP/NaOH-treated Aβ samples were diluted to 200 μM with PBS (0.6 mL, 20 μM, pH=7.4) and agitated using a shaker (Biofree) for 30 h. The solution was diluted to 20 μM with PBS (9.9 mL, 20 mM, pH=7.4), prior to each experiment.

Fitting of $A\beta_{1-42}$ Saturation Titration Experiment

Both $A\beta_{1-42}$ and IRI-1 are virtually non-fluorescent, and a simplified formula can be used where the fluorescence intensity is directly proportional to the concentration of the ($A\beta_{1-42}$-IRI-1) complex only:

$$I = \frac{1}{2}F \times \left( ([IRI1] + N[A\beta] + K_4) - \sqrt{\left( \begin{array}{c} (([IRI1] + N[A\beta] + K_4)^2 - \\ 4N[A\beta][IRI1] \end{array} \right)} \right)$$

With F: a fluorescence proportionality factor, [IRI1]: the initial concentration of IRI-1, [Aβ]: the initial concentration of $A\beta_{1-42}$, N: the number of equivalent binding sites on the Aβ fibril relative to Aβ monomer, and $K_d$: the dissociation constant.

The results in FIG. 1D were obtained following a multi-parameter optimization of the experimental results following the fluorescence intensity at 566 nm, using a concentration of 10 μM $A\beta_{1-42}$ and incremental concentrations of IRI-1 in PBS containing 2% DMF. The slit width was set at 3/3. The best fittings were obtained for N=1/4, i.e. one binding site per 4 $A\beta_{1-42}$, consistent with the hypothesized high affinity cross-β-sheet binding site on the protein fibril.

Cell Viability Assay

Cell viability was assessed by the MTT (3-4,5-dimethylthiazol-2-yl)-2,5-diphenyltetrazolium bromide) assay. SH-SY5Y cells ($1\times10^4$ per well) were treated with various concentrations of IRI-1 in a 96-well plate for 24 h at 37° C.

BBB-Penetrability PAMPA Assay

The BBB-PAMPA was conducted following the manufacturer's instructions (pION, Inc, MA, USA). Briefly, IRI-1 and Thioflavin T, were respectively diluted in donor buffer (pH 7.4) to be 12.5 UM and added at a volume of 200 μL in lower bottom of 96 well PAMPA sandwich plate. References progesterone and theophylline were similarly added at a concentration of 50 μM. The transmembrane side to the donor part was coated with BBB-lipid solution and 200 μL acceptor buffer was added in the upper chambers of the PAMPA sandwich plate. After incubation for 4 h at 25° C., all samples were transferred to a new U.V plate and then the U.V spectra were measured at a wavelength from 250 nm to 498 nm with a multifunctional microplate reader (Tecan, Infinite M200 Pro, San Jose, CA, USA) and the permeability rate (Pe, $10^{-6}$ cm/s) was determined using pION PAMPA Explorer software (ver3.8).

Brain Homogenate Preparation

Male ICR mice (10-weeks-old) from Daehan Biolink Co. Ltd. (Eumseong, Korea) were used in this experiment. The mice were accommodated at a constant temperature (23±1° C.), humidity (60±10%), and a 12 h light/dark cycle with free access to water and food. The mice were handled in accordance with the Principle of Laboratory Animal Care (NIH Publication No. 80-23; revised 1978) and the Animal Care and Use Guidelines of KyungHee University, Seoul, Korea (approval number: KHUASP(SE)-18-130). Mice were anesthetized with tribromoethanol (20 μL/g of body weight, Sigma Aldrich, USA) and then, the whole brain was removed quickly. After the washing with 0.1 M PBS, the brain tissue was excised by scissors and homogenized with a pellet pestles cordless motor (Sigma Aldrich, USA) in 2 mL of 0.1 M PBS (pH 7.4). The mixture was centrifuged at 1,000 g (Smart R17 Plus centrifuge, Hanil Scientific, Korea) for 15 min at 4° C. and the supernatant was collected. The pooled brain homogenates of 3 mice were collected and diluted to a final volume of 6 mL with PBS and used for fluorescence studies.

Ex Vivo Two-Photon Microscopy Imaging

Brain tissues were isolated from 11-month-old 5×FAD-Tg mice. All animal protocols were approved by the Institutional Animal Care and Use Committee (IACUC) of KyungHee University, Korea (Approval number: KHUSAP (SE)-18-123). The isolated brain was immediately frozen with dry ice and horizontally sectioned by using a surgical blade (No. 10, Reather safety razor Co., LTD, Japan). Sectioned brain tissues were immersed in a DMEM-buffered solution containing IBC 2 or IRI-1 (20 μM), and then incubated at 37° C. for different durations (0.5 h, 1 h and 2 h). After incubation, the brain tissues were washed with PBS (×3) and fixed in 4% paraformaldehyde solution until TPM imaging, using upright microscopy (Leica, Nussloch, Germany). IBC 2 and IRI-1-stained Aβ plaques displayed a strong red emission signal at a middle depth layer (~75 μm) of the sectioned tissues. TPM images were obtained by collecting the fluorescence from an emission channel of 580-779 nm. To compare the plaque and background signal of IBC 2 and IRI-1, TPM images analyzed by using Leica software.

Statistical Analysis of Ex Vivo Tissue Slice Data

15 Aβ-plaque regions as well as 15 background regions were randomly chosen for each dye at each incubation time. Bootstrap resampling (n=100,000) was performed on the 15 Aβ and background samples to estimate the population distribution of the signal to background ratios for each of the dyes at the different incubation times as well as to estimate the significance level of the difference of these population distributions.

Cranial Surgery and In Vivo Two-Photon Microscopy Imaging

All animal studies and maintenance were approved by the Institutional Animal Care and Use Committee (IACUC) of Seoul National University, Korea. 10-12-month-old 5×FAD (Tg6799; Jackson Lab Stock No. 006554) AD model mice were anesthetized with the mixture of Tiletamine-Zolazepam (Virbac, France) and Xylazine (Bayer Korea, Korea) via intramuscular (IM) injection (1.2 mg $kg^{-1}$) and then fixed on a customized stereotactic heating plate (37° C., Live cell instrument, Seoul, Korea). The mouse scalp was sterilized with Povidone Iodine (Firson, Korea) and then removed. A drop of Epinephrine was applied to the incision site to relieve local pain and bleeding. The periosteum was also removed in this step. When the scalp and periosteum were clearly removed and the skull dried, a small hole (3 mm diameter) was carefully made in the parietal bone with a microdrill. A 5 mm round coverslip was attached to the surgery site with Loctite 454 and dental acrylate was applied around the site. A solution of IRI-1 in 25% DMSO/PBS (5 mg kg-1) was injected intraperitoneally (i.p.) before TPM imaging. TPM live imaging was conducted using an LSM 7 MP two-photon laser-scanning microscope (Carl Zeiss Microscopy GmbH, Germany) equipped with a Chameleon-Ultra-II laser system (Coherent, USA). An appropriately tuned laser (780-920 nm wavelength, 30 mW intensity) was applied to the imaging site transiently. Emission signals were obtained through the red channel (555-610 nm), or blue channel (485-490 nm) NDD filter set. TPM images were processed and 3D reconstructed using Volocity Software (Perkin-Elmer, Waltham, MA, USA).

Synthesis of Compounds

The compound (IRI-1) represented by Formula 2 and the compound (Final-2) represented by Formula 8 were synthesized according to the synthetic routes shown in FIGS. 25 and 26, respectively.

1. Synthesis of IRI-1

(1) Synthesis of Compound 2

4-bromosalicylaldehyde (500 mg, 2.5 mmol) and 4-(dimethylamino)phenylboronic acid (534 mg, 3.2 mmol) were dissolved in 60 mL of a mixture of 1,2-dimethoxyethane/$Na_2CO_2$ 2 M 35:25 (v/v). After argon bubbling for 30 min, Pd $(PPh_3)_4$ (287 mg, 0.25 mmol, 0.1 equiv.) was added and the reaction mixture was stirred at 90° C. overnight. The reaction mixture was allowed to cool to room temperature, was transferred to a separation funnel and 100 mL brine was added. The mixture was extracted with EtOAc (3×100 mL) and the combined organic layers were dried over anhydrous $Na_2SO_4$, filtered and concentrated under reduced pressure. The crude was purified by silica column chromatography (EtOAc/n-Hexane, 1:7) to afford Compound 2 as a yellow solid (512 mg, 85%).

$^1$H NMR ($CDCl_3$, 500 MHz): § 3.03 (s, 6H, $CH_3$), 6.78 (d, J=9.0 Hz, 2H, CH), 7.17-7.18 (m, 1H, CH), 7.24 (dd, J=8.1 Hz, J=1.8 Hz, 1H, CH), 7.54 (d, J=8.1 Hz, 1H, CH), 7.58 (d, J=9.0 Hz, 2H, CH), 8.85 (d, J=0.6 Hz, 2H, CH), 8.85 (d, J=0.6 Hz, 1H, OH), 11.15 (s, 1H, CH) ppm; $^{13}$C NMR ($CDCl_3$, 125 MHz): δ 40.31, 112.38, 113.86, 117.70, 118.67, 126.33, 128.16, 134.01, 149.90, 151.02, 162.13, 195.53 ppm. MS (ESI): $C_{15}H_{15}NO_2$ $[M]^+$, m/z calcd 241.11, found 241.95.

(2) Synthesis of IRI-1

Piperidine (1 drop) was added to a mixture of Compound 2 (398 mg, 1.7 mmol) and malononitrile (120 mg, 1.8 mmol) in absolute ethanol (40 mL). The reaction mixture was stirred at room temperature for 2 h. The solvent was evaporated under reduced pressure, and the crude product was recrystallized from ethanol to afford IRI-1 as an orange solid (420 mg, 88%).

$^1$H NMR (DMSO-$d_6$, 500 MHz): δ 2.97 (s, $CH_3$, 6H), 6.79 (d, 2H, CH, J=8.9 Hz), 7.37 (s, CH, 1H), 7.50-7.60 (m, 2H, CH), 7.66 (d, J=8.9 Hz, 2H, $CH_2$), 8.33 (s, 1H, CH), 8.72 (s, 1H, NH) ppm; $^{13}$C NMR (DMSO-$d_6$, 125 MHz): §

102.60, 111.58, 112.83, 115.55, 116.10, 121.56, 125.05, 128.19, 130.33, 146.53, 147.11, 151.30, 152.44, 154.99 ppm [$N(CH_3)_2$ was not observed, presumed to be underneath the solvent peak]. MS (ESI): $C_{18}H_{15}N_3O$ $[M+H]^+$, m/z calcd 289.12, found 290.15.

2. Synthesis of Final-2

(1) Synthesis of Compound 4

2-bromofuran (3.8 g, 25.8 mmol) and 4-(dimethylamino) phenylboronic acid (5.546 g, 33.6 mmol) were dissolved in 95 mL of a mixture of 1,2-dimethoxyethane/$Na_2CO_2$ 2 M 50:45 (v/v). After argon bubbling for 30 min, $Pd(PPh_3)_4$ (2.988 g, 2.6 mmol, 0.1 equiv.) was added and the reaction mixture was stirred at 90° C. overnight. The reaction mixture was allowed to cool to room temperature, was transferred to a separation funnel and 100 mL brine was added. The mixture was extracted with EtOAc (3×100 mL) and the combined organic layers were dried over anhydrous $Na_2SO_4$, filtered and concentrated under reduced pressure. The crude was purified by silica column chromatography (EtOAc/n-Hexane, 1:7) to afford Compound 4 as a white solid (4.358 g, 90%).

$^1H$ NMR ($CDCl_3$, 500 MHz): § 2.99 (s, 6H, $CH_3$), 6.36-6.45 (m, 2H, CH), 6.74 (d, J=8.8 Hz, 2H, $CH_2$), 7.26 (m, 1H, CH), 7.55 (d, J=8.8 Hz, 2H, $CH_2$) ppm.

(2) Synthesis of Compound 5 n-BuLi (5.450 mL, 14.6 mmol) was added to a mixture of anhydrous tetrahydrofuran (100 mL) and Compound 4 (1.104 g, 5.9 mmol) stirred at −78° C. Thereafter, the temperature of the reaction mixture was slowly adjusted to −40° C., followed by stirring for 1 h. The reaction mixture was again cooled to −78° C. and 4,4,5,5-tetramethyl-2-(propan-2-yloxy)-1,3,2-dioxaborolane (2.406 mL, 11.8 mmol) was added dropwise thereto. After the reaction mixture was allowed to rise to room temperature, the reaction was quenched with $NH_4Cl$ solvent. The mixture was extracted with EtOAc (3×100 mL) and the combined organic layers were dried over anhydrous $Na_2SO_4$, filtered, and concentrated under reduced pressure. The crude was purified by silica column chromatography (EtOAc/n-Hexane, 1:9) to afford Compound 5 as a white solid (818 mg, 44%).

$^1H$ NMR ($CDCl_3$, 500 MHz): δ 2.98 (s, 6H, $CH_3$), 6.32 (d, J=3.3 Hz, 1H, CH), 6.38 (d, J=3.3 Hz, 1H, CH), 6.71 (d, J=9.0 Hz, 2H, $CH_2$), 7.49 (d, J=9.0 Hz, 2H, $CH_2$) ppm.

(3) Synthesis of Compound 6

4-bromosalicylaldehyde (1.108 g, 5.5 mmol) and Compound 5 (1.438 g, 4.6 mmol) were dissolved in 60 mL of a mixture of 1,2-dimethoxyethane/$Na_2CO_2$ 2 M 35:25 (v/v). After argon bubbling for 30 min, $Pd(PPh_3)_4$ (531 mg, 0.46 mmol, 0.1 equiv.) was added and the reaction mixture was stirred at 90° C. overnight. The reaction mixture was allowed to cool to room temperature, was transferred to a separation funnel and 100 mL brine was added. The mixture was extracted with EtOAc (3×100 mL) and the combined organic layers were dried over anhydrous $Na_2SO_4$, filtered and concentrated under reduced pressure. The crude was purified by silica column chromatography (EtOAc/n-Hexane, 1:9) to afford Compound 6 as an orange solid (317 mg, 22%).

$^1H$ NMR ($CDCl_3$, 500 MHz): δ 2.98 (s, 6H, $CH_3$), 6.79 (d, J=9.0 Hz, 2H, $CH_2$), 6.85 (d, J=3.6 Hz, 1H, CH), 7.22 (d, J=3.6 Hz, 1H, CH), 7.33 (d, J=1.4 Hz, 1H, CH), 7.35 (dd, J=1.4 Hz, J=8.2 Hz, 1H, CH), 7.64 (d, J=9.0 Hz, 2H, $CH_2$), 10.17 (s, 1H, CH) ppm.

(4) Synthesis of Final-2

Piperidine (1 drop) was added to a mixture of Compound 6 (100 mg, 0.33 mmol) and malononitrile (24 mg, 0.36 mmol) in absolute ethanol (50 mL). The reaction mixture was stirred at room temperature for 2 h. The solvent was evaporated under reduced pressure, and the crude product was recrystallized from ethanol to afford Final-2 as a red solid (84 mg, 72%).

$^1H$ NMR (DMSO-$d_6$, 500 MHz): § 2.97 (s, $CH_3$, 6H), 6.78 (d, J=8.8 Hz, 2H, $CH_2$), 6.87 (d, J=3.6 Hz, 1H, CH), 7.34 (d, J=3.6 Hz, 1H, CH), 7.48 (s, 1H, CH), 7.56-7.75 (m, 4H), 8.32 (s, 1H, CH), 8.78 (s, 1H, NH) ppm; $^{13}C$ NMR (DMSO-$d_6$, 125 MHz): δ 40.33, 102.80, 106.02, 109.09, 112.58, 113.21, 116.06, 116.24, 117.92, 119.15, 125.65, 130.62, 135.64, 146.81, 149.66, 150.62, 152.24, 154.96, 156.30 ppm.

Results and Discussion

In the present invention, novel intramolecular rotation-enabled two-photon fluorescent probe compounds represented by Formula 1 were synthesized to solve the problems of the previously described probes. In each of the two-photon fluorescent probe compounds represented by Formula 1, a twisted intramolecular charge state (TICT)-based fluorescence quenching pathway was introduced, which resulted in a remarkable fluorescence increase of 167-fold in response to Aβ proteins, while maintaining an excellent two-photon fluorescence cross-section. In addition, the two-photon fluorescent probe compounds represented by Formula 1 were found to have high signal-to-noise ratios.

In order to maintain excellent BBB penetrability, a neutral molecule with an intermediate lipophilicity was designed, which adopts a hybrid structure between IBC 2 and ThT. As a representative example, IRI-1 represented by Formula 2 was synthesized (see FIG. 25). Specifically, IRI-1 was synthesized through a Suzuki coupling reaction between 4-bromosalicylaldehyde and 4-(dimethylamino)phenylboronic acid, followed by a condensation and cyclization reaction with malononitrile (FIG. 25). The key structural and predicted physicochemical properties of IRI-1 were compared with the BBB penetrability selection rules introduced by Hitchcock et al. (S. A. Hitchcock, L. D. Penington, J. Med. Chem. 206, 49, 759-7583), with the results indicating a good probability of adequate BBB penetrability (Table 1). A BBB parallel artificial membrane permeability assay (PAMPA) for IRI-1 also demonstrated a good BBB penetrability (Table 2).

TABLE 1

| | Selection rule | IRI-1 |
|---|---|---|
| Topological polar surface area (TPSA)[a] | <90 Å$^2$ | 64 Å$^2$ |
| H-bond donors | ≤3 | 1 |
| Calculated logP[b] | 2-5 | 3.30 ± 0.49 |
| Calculated logD[c] | 2-5 | 3.30 ± 0.49 |
| Molecular weight | ≤500 Da | 289.33 Da |

[a]Calculatated using the Molinspiration applet.
[b]Calculated from pooled logP data, as implemented by the ALOGPS 2.1 applet.
[c]IRI-1 is neutral at physiological pH (See FIG. S10), thus logD = logP.

[a]Calculated using the Molinspiration applet. [b]Calculated from pooled log P data, as implemented by the ALOGPS 2.1 applet. [c]IRI-1 is neutral at physiological pH (See Figure S10), thus log D=log P.

TABLE 2

| Compound | $P_e$ ($10^{-6}$ cm/s) | Permeability classification[b] |
|---|---|---|
| Progesterone[a] | 39.45 ± 5.593[c] | High |
| Theophylline[a] | 0.250 ± 0.023[c] | Low |
| IRI-1 | 0.562 ± 0.053[c] | High |
| Thioflavin T | 0[c] | Not permeable |

[a]Assay references.
[b]High permeability (as indicated by the PAMPA supplier): $P_e > 0.4 \times 10^{-6}$ cm/s.
[c]Mean and standard deviation, n = 3.

The absorbance, emission and fluorescence quantum yield of IRI-1 were determined in relation to the physical properties of 14 low-viscosity solvents. As can be seen from Table 3 and FIG. 5, the Stokes' shift increased and the quantum yield of fluorescence decreased with increasing solvent polarity. The very large Stokes' shifts (up to 211 nm) are consistent with an intramolecular charge transfer process. The probe's fluorescence intensity was largely independent of solvent viscosity. In high-viscosity solvents, a clear fluorescence increase with increasing viscosity can be seen (FIG. 6). This indicates the involvement of molecular motion, presumed to be rotation between the dimethylaniline pendant and the coumarin core, in the non-emissive de-excitation of IRI-1 in high-polarity, low-viscosity solvents.

TABLE 3

| | IRI-1 | | | | Solvent | Solvent |
|---|---|---|---|---|---|---|
| | $\lambda_{Abs}$ (nm) | $\lambda_{Em}$ (nm) | $\Delta\lambda$ (nm) | $\Phi_{Fl}$[a] (%) | viscosity (cP) | dielectric constant |
| Acetone | 417 | 628 | 211 | 9.6 | 0.32 | 20.7 |
| Acetonitrile | 416 | 624 | 208 | 7.0 | 0.37 | 37.5 |
| 1-Butanol | 425 | 614 | 189 | 9.9 | 2.95 | 17.8 |
| Chloroform | 429 | 559 | 130 | 96.4 | 0.58 | 4.81 |
| 1,2-Dichlorobenzene | 436 | 572 | 136 | 93.2 | 1.32 | 9.93 |
| Diethyl ether | 409 | 631 | 123 | 74.3 | 0.24 | 4.34 |
| N,N-Dimethylformamide | 422 | 630 | 208 | 5.2 | 0.92 | 36.70 |
| Ethanol | 425 | 630 | 205 | 1.5 | 1.10 | 24.55 |
| Ethyl acetate | 412 | 575 | 163 | 72.3 | 0.46 | 6.02 |
| Ethylene glycol dimethyl ether | 415 | 600 | 185 | 36.9 | 0.46 | 7.20 |
| Methanol | 422 | 630 | 208 | 5.8 | 0.55 | 32.60 |
| 1-Propanol | 425 | 622 | 197 | 10.5 | 2.26 | 20.1 |
| Tetrahydrofuran | 417 | 569 | 152 | 32.7 | 0.55 | 7.60 |
| Toluene | 417 | 506 | 89 | 86.3 | 0.59 | 2.40 |

[a]Determined vs. 4-(Dicyanomethylene)-2-methyl-6-(4-dimethylaminostyryl)-4H-pyran in acetonitrile.

An absorbance maximum in the presence of Aβ fibrils can be observed at 419 nm (FIG. 1A), and the dye exhibits a fluorescence maximum at 566 nm ($\lambda_{ex}$=405 nm, FIG. 1B). In the absence of Aβ fibrils, virtually no emission was observed in PBS (FIG. 1B), thus indicating the ability of Aβ fibrils to increase the fluorescence by two potential pathways: reduced polarity and conformational restriction at the protein binding site. In PBS, the dye existed as a monomer up to a concentration of 4.7 μM, after which soluble aggregates are formed (FIG. 7). The absorbance and emission maxima of IRI-1 bound to Aβ are a close match with those in tetrahydrofuran, thus suggesting a relatively apolar environment at the protein binding site.

Also for Final-2, an absorbance maximum in the presence of Aβ fibrils can be observed at 465 nm. The dye exhibits a fluorescence maximum at 639 nm ($\lambda_{ex}$=465 nm, FIG. 24). In the absence of Aβ fibrils, virtually no emission was observed in PBS, thus indicating that the dye effectively responds to Aβ fibrils, resulting in an increase in fluorescence, despite the increased number of intramolecular rotatable bonds.

The fluorescent response of IRI-1 to potential interferants, such as metal ions, amino acids, and thiols (FIG. 1C) showed no or negligible fluorescence enhancement. The absorbance of the dye was recorded in the pH 2-10 range and demonstrated a ratiometric shift with a $pK_a$ of 4.22±0.12 (FIG. 8B), while no additional transitions were observed at higher pH values. Thus, the fluorophore is not charged under physiological conditions (cf. calculated Log D, FIG. 9). Moreover, IRI-1 showed only relatively weak fluorescence enhancement in the presence of bovine serum albumin (BSA), human serum albumin (HSA), or mouse brain homogenates (FIG. 10). The binding affinity of IRI-1 toward Aβ fibrils was Kd=374±115 nm, as determined using nonlinear fitting (FIG. 1D). This is approximately two-to three-folds stronger than previously reported for ThT (W. E. Klunk, Y. Wang, G.-f. Huang, M. L. Debnath, D. P. Holt, C. A. Mathis, Life Sci. 201, 69, 1471-1484), which is consistent with the non-charged nature of IRI-1. A solution of the probe in dimethylformamide (DMF) showed a relatively high resistance to photobleaching (FIG. 11).

In the presence of Aβ fibrils, IRI-1, ThT, and IBC-2 show fluorescence enhancement of 167-fold, 20-fold, and 2.5-fold, (D. Kim et al., ACS Cent. Sci. 2016, 2, 967-975) respectively (FIG. 1B and FIG. 12), thus clearly demonstrating the importance of introducing the molecular rotor concept to minimize off-target fluorescence.

The two-photon cross-section of IRI-1 reaches values of up to 111 GM (Goeppert-Mayer) at an excitation wavelength of 880 nm (FIG. 13). This clearly demonstrates that IRI-1 retained the excellent two-photon properties of both ThT and IBC-2, while enabling very strong fluorescence enhancement due to virtually fully quenched fluorescence in the absence of the target protein.

In order to rationalize the polarity and viscosity-responsive behavior of IRI-1, theoretical calculations were performed, with a focus on the solvent-dependent exited-state behavior of the probe, and the solvatochromic response. The calculations clearly indicated the involvement of TICT in the non-emissive de-excitation of IRI-1 in polar solvents, while suggesting the population of an emissive locally excited state in solvents of lower polarity, thus rationalizing the observations above (FIG. 2).

Recently, a near-atomic-resolution cryo-EM structure of $A\beta_{1-42}$ was reported (PDB ID: 50QV) (L. Gremer et al., Science 2017, 358, 16-19) and this structure was used as the protein scaffold for docking studies here. Since the conformation of $Phe^{20}$ was not unambiguously determined, docking studies were performed for the two possible conformations separately. Two major interaction locations were identified for IRI-1 with similar predicted binding affinities.

The first binding site is a tunnel along the fibril axis, consisting of the side chains of $Phe^{19}$, $Asn^{27}$, $Gly^{29}$, and $Ile^{31}$ (FIG. 3 and FIG. 14), whereas a second binding site was located on a groove along the fibril axis on the exposed surface adjacent to $Phe^{20}$ (FIG. 3). In particular, the conformation depicted in FIG. 3A leads to the highest overall binding affinity and is consistent with a previously proposed interaction site along the ridge adjacent to $Phe^{20}$ on $A\beta_{1-40}$ (L. Jiang et al., eLife 2013, 2, e0857). Whereas docking studies are unable to pinpoint the dominant binding mode, the tunnel-based interaction may be more kinetically stable (R. Zou et al., ACS Chem. Neurosci. 2019, DOI: 10.1021/acschemneuro.8b062).

The cytotoxicity of the probe was determined in SH-SY5Y human neuroblastoma cells, and no significant toxicity at concentrations up to 50 μM was measured (FIG. 15).

Brain tissue slices isolated from 11-month-old 5×FAD-Tg mice were incubated with 20 μM IRI-1 or 20 μM IBC-2 for 30 min, 1 h, or 2 h (FIGS. 16-18). The IRI-1-treated sample (2 h) shows a remarkable absence of TPM background fluorescence as compared to an analogously treated and imaged IBC-2 sample (FIG. 4A-B). The image traces through a single Aβ plaque (FIG. 4C) also clearly show reduced background fluorescence for IRI-1.

Finally, for each dye, 15 plaques and 15 random background regions were chosen. A significant difference in fluorescence ratios between IRI-1- and IBC-2-treated samples was found in the samples treated for 1 h or 2 h (FIGS. 19-21 and FIG. 4D). After 2 h incubation, the signal-to-background ratio for IRI-1-treated brain slices was approximately 3.75-fold elevated compared to IBC-2 (FIG. 4D), thus strongly suggesting that the addition of a TICT deactivation mechanism to quench the fluorescence in the unbound state is highly beneficial to the overall image signal-to-background ratio.

Having confirmed that IRI-1 brightly labels Aβ plaques while suppressing background fluorescence, the behavior of IRI-1 in vivo upon injection in the peritoneal cavity was subsequently investigated. Fluorescence enhancement of Aβ plaques in the frontal cortex of 10-12-month-old 5×FAD-Tg mice was observed, reaching full saturation after approximately 40 min (FIG. 22), thus demonstrating good BBB penetration. Excitation at 920 nm was found to result in the brightest emission due to the combined lower tissue background emission and good two-photon cross-sections of IRI-1.

To confirm the nature of the fluorescently labelled species in vivo, in a second experiment, IRI-1 was co-administered with the well-known Aβ-plaque-specific two-photon fluorescent dye MeO—X04 (W. E. Klunk et al., J. Neuropathol. Exp. Neurol. 202, 61, 797-805). The excitation and emission windows of the two dyes showed no spectral overlap (FIG. 23). As can be seen in FIG. 4E-J, co-administration experiments revealed near perfect overlap between images obtained with MeO—X04 or IRI-1. IRI-1 was found to clearly visualize Aβ deposits on cerebral blood vessels associated with cerebral amyloid angiopathy (CAA) as well (FIG. 4H-J). Finally, 3D two-photon imaging with IRI-1 in 5×FAD-Tg mice in vivo revealed that individual Aβ plaques could be detected up to a depth of 172 mm (FIG. 4K).

In summary, it was demonstrated that the introduction of the molecular-rotor concept to an Aβ plaque sensing dye significantly minimizes background fluorescence. In practice, the two-photon fluorescent probe compound of the present invention shows efficient BBB penetration and high selectivity and sensitivity for Aβ plaques. This demonstrated that the addition of the molecular rotor concept results in increased signal-to-background ratios both in solution and in complex biological matrixes such as brain tissues. Therefore, the two-photon fluorescent probe compound of the present invention could find applications in the field of neurodegenerative research, including the early diagnosis and treatment of AD.

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

INDUSTRIAL APPLICABILITY

The two-photon fluorescent probe compound of the present invention can be used to effectively image Aβ plaques due to its high selectivity and sensitivity for Aβ plaques. Therefore, the two-photon fluorescent probe compound of the present invention could find applications in the field of neurodegenerative research, including the early diagnosis and treatment of Alzheimer's disease.

The invention claimed is:

1. A two-photon fluorescent probe compound selected from the compounds represented by Formulae 2, 4, and 6 to 13:

[Formula 2]

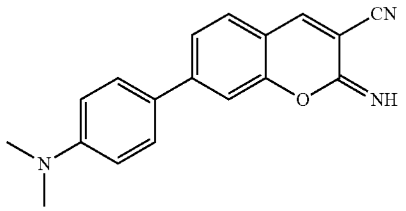

[Formula 4]

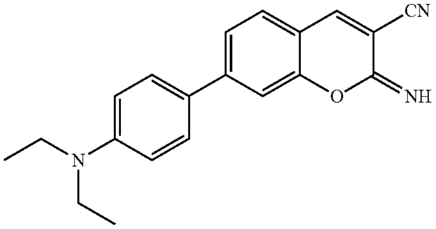

[Formula 6]

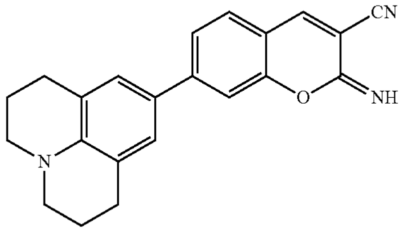

[Formula 7]

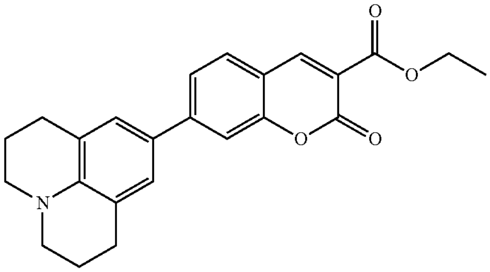

[Formula 8]

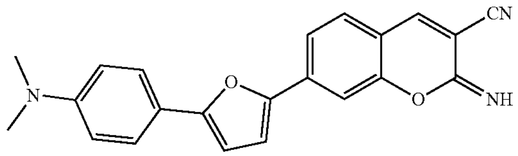

-continued

[Formula 9]

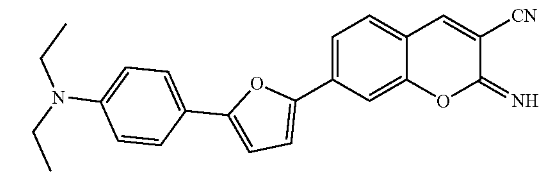

[Formula 10]

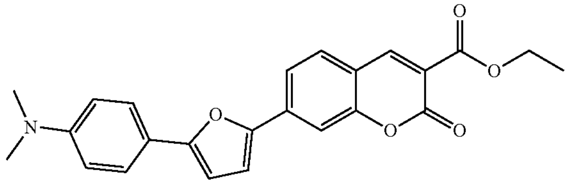

[Formula 11]

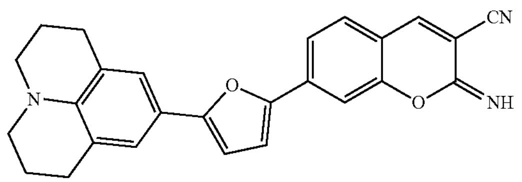

-continued

[Formula 12]

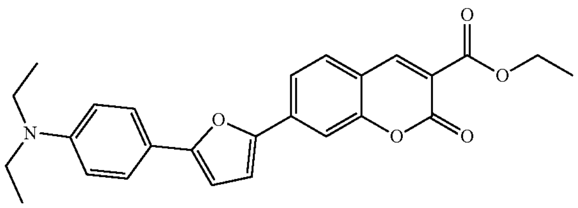

[Formula 13]

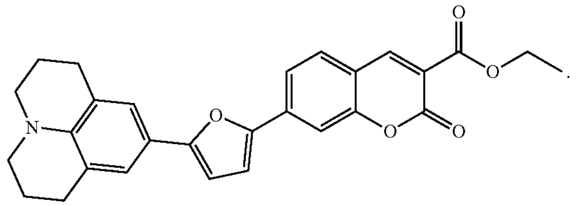

2. The two-photon fluorescent probe compound according to claim 1, wherein the two-photon fluorescent probe compound specifically binds to amyloid beta plaques.

3. A composition for detecting amyloid beta comprising the two-photon fluorescent probe compound according to claim 1.

4. A method for imaging amyloid beta plaques, comprising: injecting the two-photon fluorescent probe compound according to claim 1 into a sample isolated from a living body; allowing the two-photon fluorescent probe compound to bind to amyloid beta plaques in the sample; irradiating an excitation source onto the sample; and monitoring fluorescence generated from the two-photon fluorescent probe compound with a two-photon microscope.

5. The method according to claim 4, wherein the sample isolated from a living body is a cell or tissue sample.

* * * * *